United States Patent
Humeniuk

(10) Patent No.: US 9,336,352 B2
(45) Date of Patent: May 10, 2016

(54) POWER INJECTOR WITH HELP FUNCTIONALITY

(75) Inventor: David P. Humeniuk, Cincinnati, OH (US)

(73) Assignee: LIEBEL-FLARSHEIM COMPANY LLC, Hazelwood, MO (US)

( * ) Notice: Subject to any disclaimer, the term of this patent is extended or adjusted under 35 U.S.C. 154(b) by 283 days.

(21) Appl. No.: 12/676,968

(22) PCT Filed: Feb. 27, 2009

(86) PCT No.: PCT/US2009/035366
§ 371 (c)(1),
(2), (4) Date: Mar. 8, 2010

(87) PCT Pub. No.: WO2009/114285
PCT Pub. Date: Sep. 17, 2009

(65) Prior Publication Data
US 2011/0016392 A1  Jan. 20, 2011

Related U.S. Application Data

(60) Provisional application No. 61/035,518, filed on Mar. 11, 2008.

(51) Int. Cl.
*G06F 19/00* (2011.01)
*A61M 5/145* (2006.01)
*A61B 6/00* (2006.01)

(52) U.S. Cl.
CPC ....... *G06F 19/3406* (2013.01); *A61M 5/14546* (2013.01); *A61B 6/548* (2013.01); *A61M 2005/14553* (2013.01); *A61M 2205/502* (2013.01); *G06F 19/321* (2013.01)

(58) Field of Classification Search
CPC .............. G06F 19/321; G06F 19/3487; G06Q 10/0633

USPC .......................................................... 715/705
See application file for complete search history.

(56) References Cited

U.S. PATENT DOCUMENTS

| | | | | |
|---|---|---|---|---|
| 5,814,015 A | * | 9/1998 | Gargano | A61M 5/1456 604/151 |
| 2004/0095372 A1 | * | 5/2004 | Berry | G06F 3/0481 715/713 |
| 2006/0079768 A1 | * | 4/2006 | Small | A61M 5/14546 600/432 |

(Continued)

FOREIGN PATENT DOCUMENTS

| WO | 2006044409 A2 | 4/2006 |
|---|---|---|
| WO | 2007050771 | 5/2007 |
| WO | 2007062315 A2 | 5/2007 |

*Primary Examiner* — Sherrod Keaton
(74) *Attorney, Agent, or Firm* — Marsh Fischmann & Breyfogle LLP

(57) ABSTRACT

A power injector (10) with help functionality is disclosed. What may be characterized as a 'help output' may be displayed on a graphical user interface (11) in response to a request for help. This help output may be based upon a current state of the power injector (10), may be accompanied by a cross-reference to an operator's manual for the power injector (10), may be expanded to provide additional detail, or any combination thereof. At least one system screen that relates to the help output may be displayed (e.g., simultaneously, sequentially). The help functionality may be in the form of having the power injector (10) incorporate help mode logic (256) that is configured to allow a user to view and obtain information on the various system screens that would be presented when using the power injector (10) to deliver a fluid, but without actually operating the power injector (10) to deliver fluid.

17 Claims, 12 Drawing Sheets

(56) References Cited

U.S. PATENT DOCUMENTS

| | | | |
|---|---|---|---|
| 2007/0027733 A1* | 2/2007 | Bolle | G06F 19/321 705/7.13 |
| 2007/0100282 A1 | 5/2007 | Small et al. | |
| 2008/0059961 A1* | 3/2008 | Miranda-Steiner | G06F 9/4446 717/171 |
| 2009/0036764 A1* | 2/2009 | Rivas et al. | 600/365 |

\* cited by examiner

POWER INJECTOR WITH HELP FUNCTIONALITY

RELATED APPLICATIONS

This application is a U.S. National Stage of PCT/US2009/035366, filed 27 Feb. 2009, which claims priority to and is a non-provisional application of U.S. provisional application Ser. No. 61/035,518 filed on 11 Mar. 2008 and entitled "POWER INJECTOR WITH HELP FUNCTIONALITY". Priority is claimed to each patent application set forth in this Related Applications section.

FIELD OF THE INVENTION

The present invention generally relates to the field of power injectors, and, more particularly, to providing assistance on one or more aspects of the operation/usage of power injectors.

BACKGROUND

Various medical procedures require that one or more medical fluids be injected into the patient. Medical imaging procedures oftentimes involve the injection of a contrast media into the patient, possibly along with saline or other fluids. Other medical procedures involve injecting one or more fluids into a patient for therapeutic purposes. Power injectors may be used for these types of applications.

A power injector generally includes what is commonly referred to as a powerhead. One or more syringes may be mounted to the powerhead in various manners (e.g., detachably; rear-loading; front-loading). Each syringe typically includes what may be characterized as a syringe plunger, piston, or the like. Each such syringe plunger is designed to interface with (e.g., contact and/or temporarily interconnect with) an appropriate syringe plunger drive assembly that is incorporated into the powerhead, such that operation of the syringe plunger drive assembly axially advances the associated syringe plunger inside and relative to a barrel of the syringe. One typical syringe plunger drive assembly is in the form of a ram that is mounted on a threaded lead screw or drive screw. Rotation of the lead screw in one rotational direction advances the associated ram in one axial direction, while rotation of the lead screw in the opposite rotational direction advances the associated ram in the opposite axial direction.

An operators manual, a service manual, or the like may be made available for a given power injector model. The operators manual may provide valuable information regarding setting up and/or operating a power injector for an injection procedure. It is of course advisable for users of power injectors to become and maintain their familiarity with the relevant power injector. This may be done through periodically reviewing the operators manual and other documentation that may be provided by the power injector manufacturer, particularly when being used for an injection procedure. Owners of such power injectors may also require that personnel that use their power injectors obtain periodic training, which not only may reduce the potential for operating the power injector in an un-safe manner, but which also may increase the potential that the various features incorporated into the design of the power injector are being fully utilized by such personnel.

SUMMARY

A first aspect of the present invention is embodied by a power injector that includes a powerhead, a syringe plunger drive assembly, and a first graphical user interface. A syringe may be installed on the powerhead and may be designed to interface or interact with the syringe plunger drive assembly in any appropriate manner. A first help output is presentable on the first graphical user interface. At least one cross-reference to this first help output is also presentable on the first graphical user interface.

Various refinements exist of the features noted in relation to the first aspect of the present invention. Further features may also be incorporated in the first aspect of the present invention as well. These refinements and additional features may exist individually or in any combination in relation to the first aspect. Initially, the various features addressed below in relation to one or more of the second and third aspects may be utilized by this first aspect, individually or in any desired combination.

The first help output may be in the form of a first help topic, and at least one cross-reference may be presented on the first graphical user interface in the form of at least one system screen that relates to this first help topic. This "system screen" may be a screen that is presented on the first graphical user interface during operation of the power injector to deliver fluid. In one embodiment, at least one system screen that relates to the first help topic may be selectively presented on the first graphical user interface after the first help topic has been presented. In another embodiment, at least one system screen that relates to the first help topic may be simultaneously presented with the first help topic on the first graphical user interface. In yet another embodiment, each system screen that relates to the first help topic may be presented on the first graphical user interface (e.g. simultaneously; sequentially).

At least one cross-reference to the first help output may be presented on the first graphical user interface in the form of an identification of at least one section of an operator's manual for the power injector that pertains to the first help output, and including an identification of each applicable section of the operators manual. In one embodiment, this identification allows a user to retrieve a hard copy of the operator's manual and to proceed to at least one relevant section thereof. At least one cross-reference to the first help output may be presented on the first graphical user interface in the form of a link to a least one section of an operators manual for the power injector that pertains to the first help output, and including a link to each applicable section of the operator's manual. The operators manual may be electronically stored, such that "clicking" or "selecting" an electronic link may direct a user to the relevant section or sections of the operators manual.

The first help output that is presented on the first graphical user interface may be of a first level of help information. A cross-reference to the first help output that may be presented on the first graphical user interface may be of a second level of help information that is more detailed than that encompassed by the first help output. In one embodiment, a cross-reference to the first help output is an expanded or more detailed version of the content provided by the first help output. This expanded help information may be generated in any appropriate manner, including be selecting or activating an "expand" button, icon, or the like.

A second aspect of the present invention is embodied by a power injector that includes a powerhead, a syringe plunger drive assembly, and a first graphical user interface. A syringe may be installed on the powerhead and may be designed to interface or interact with the syringe plunger drive assembly in any appropriate manner. A first help output is presentable on the first graphical user interface, and this first help output is based upon a current state of the power injector.

Various refinements exist of the features noted in relation to the second aspect of the present invention. Further features may also be incorporated in the second aspect of the present invention as well. These refinements and additional features may exist individually or in any combination in relation to the second aspect. Initially, the various features addressed above in relation to the first aspect, as well as the various features that will be addressed below in relation to the third aspect, may be utilized by this second aspect, individually or in any desired combination.

The current state of the power injector may be monitored or determined in any appropriate manner. Representative power injector states for purposes of this second aspect include without limitation that the power injector is powered on and that no syringes are installed on the powerhead, that at least one syringe is installed on the powerhead, that the powerhead is in a tilted up position, that an air purge operation is being executed, that an air purge operation has been completed, that the powerhead is in a tilted down position, that the power injector is ready to be enabled, that the power injector is enabled, that a patency check injection is being executed, that a patency check has been completed, that a drip mode injection is being executed, that a drip mode injection has been terminated, that a timing bolus injection is being executed, that a timing bolus injection has been completed, that an injection is being executed, that an injection has been interrupted, that an injection has failed, that an injection has been completed, that each syringe has been removed from the powerhead, that a "return each syringe plunger driver to a home position" operation is being executed, and that the power injector is ready to accept a number of syringes for which the power injector is configured.

A third aspect of the present invention is embodied by a power injector that includes a powerhead, a syringe plunger drive assembly, and a first graphical user interface. A syringe may be installed on the powerhead and may be designed to interface or interact with the syringe plunger drive assembly in any appropriate manner. This power injector further includes power injector control logic, which in turn includes fluid delivery logic and help mode logic. The power injector may be operated in accordance with the fluid delivery logic to deliver fluid. The power injector may also be operated in accordance with the help mode logic, where fluid is not delivered by the power injector. As such, the help mode logic may be characterized as a tutorial mode or the like.

Various refinements exist of the features noted in relation to the third aspect of the present invention. Further features may also be incorporated in the third aspect of the present invention as well. These refinements and additional features may exist individually or in any combination in relation to the third aspect. Initially, the various features discussed above on the first aspect may be utilized by this third aspect, individually or in any desired combination.

When the power injector is operated in accordance with the help mode logic, at least one system screen is presentable on the first graphical user interface. This system screen is one that is utilized when the power injector is operated in the fluid delivery mode, and may be selected or retrieved in any appropriate manner. Selecting a selectable object from any such system screen presents a first help output on the first graphical user interface. Any appropriate selectable object may be included on a system screen. Multiple, selectable objects may be included on any such system screen. Any appropriate number of selectable objects may be included on any such system screen. In one embodiment, each system screen that is presented when the power injector is operated in the fluid delivery mode, is also presentable on the first graphical user interface when the power injector is operated in accordance with the help mode logic. For instance, a user may be able to scroll through the various system screens, and may be able to retrieve help information on the various parameters, data, designations, and buttons or keys included on the system screen.

A fourth aspect of the present invention is embodied by a method for operating a power injector. Help may be requested on at least one aspect of the power injector. A first help output is displayed on a first graphical user interface in response to this request. At least one cross-reference to the first help output is displayed on the first graphical user interface (e.g., simultaneously with the first help output; sometime after the first help output is displayed). The various features addressed above in relation to the first aspect may be utilized by this fourth aspect, individually or in any desired combination.

A fifth aspect of the present invention is embodied by a method for operating a power injector. A state of the power injector is determined. Help may be requested on at least one aspect of the power injector. A first help output is presented on a first graphical user interface in response to this request, and this first help output is based upon the current state of the power injector. The various features addressed above in relation to the second aspect may be utilized by this fifth aspect, individually or in any desired combination.

A sixth aspect of the present invention is embodied by a method for operating a power injector. This power injector may be operated at least in each of a fluid delivery mode and a help mode. The power injector delivers a fluid when being operated in the fluid delivery mode, but not when being operated in the help mode. When the help mode is the selected mode of operation, at least one system screen is displayed. This system screen would also be presented when the power injector is operated in the fluid delivery mode. In any case, a user may selectively display help information on each of the plurality of objects that are included on the displayed system screen. Although not required by the sixth aspect, each system screen that is displayed when the power injector is being operated in its fluid delivery mode may also be displayed when the power injector is being operated in its help mode. The various features addressed above in relation to the third aspect may be utilized by this sixth aspect, individually or in any desired combination.

A seventh aspect of the present invention is embodied by a power injector that includes a powerhead, a syringe plunger drive assembly, and a first graphical user interface. A syringe may be installed on the powerhead and may be designed to interface or interact with the syringe plunger drive assembly in any appropriate manner. The power injector also includes help logic that is configured to both display a selected help topic on the first graphical user interface, as well as at least one system screen that relates to this selected help topic. Although the help topic and any related system screen may be simultaneously displayed, the help topic and one or more related system screens may be sequentially displayed as well in the case of the seventh aspect.

An eighth aspect of the present invention is embodied by a method for operating a power injector. Help may be requested on at least one aspect of the power injector. A first help output is displayed on a first graphical user interface in response to this request. At least one system screen is displayed on the first graphical user interface that relates to this first help output (e.g., simultaneously with the first help output; sometime after the first help output has been displayed).

A ninth aspect of the present invention is embodied by a power injector that includes a powerhead, a syringe plunger drive assembly, and a first graphical user interface. A syringe may be installed on the powerhead and may be designed to interface or interact with the syringe plunger drive assembly in any appropriate manner. The power injector also includes help logic that is configured to display a selected help topic on the first graphical user interface, along with a cross-reference to at least one section of an operators manual for the power injector where this first help output is addressed (e.g., in more detail). This cross-reference may simply list the relevant section(s) of the operators manual, or may be in the form of an electronic link or the like to an electronic copy of the operators manual.

A tenth aspect of the present invention is embodied by a method for operating a power injector. Help may be requested on at least one aspect of the power injector. A first help output is displayed on a first graphical user interface in response to this request. A cross-reference to at least one section of an operator's manual for the power injector where this first help output is addressed (e.g., in more detail) is also displayed on the first graphical user interface. This cross-reference may simply list the relevant section(s) of the operators manual, or may be in the form of an electronic link or the like to an electronic copy of the operators manual.

An eleventh aspect of the present invention is embodied by a power injector that includes a powerhead, a syringe plunger drive assembly, and a first graphical user interface. A syringe may be installed on the powerhead and may be designed to interface or interact with the syringe plunger drive assembly in any appropriate manner. The power injector also includes help logic that is configured to display each of a first level of information on a selected help topic and a second level of information on this same selected help topic, where the second level of information is more detailed than the first level of information. In one embodiment, the first level of information is that which is first displayed when help is requested, followed by the second level of information in response to a request for additional or expanded help information.

A twelfth aspect of the present invention is embodied by a method for operating a power injector. Help may be requested on at least one aspect of the power injector. A first help output is displayed on a first graphical user interface in response to this request. An option is provided to acquire more detailed information on the relevant aspect of the power injector.

A thirteenth aspect of the present invention is embodied by a power injector that includes a powerhead, a syringe plunger drive assembly, and a first graphical user interface. A syringe may be installed on the powerhead and may be designed to interface or interact with the syringe plunger drive assembly in any appropriate manner. The power injector also includes help logic, along with a help button or the like that is included on a screen currently being displayed on the first graphical user interface. The help logic may be configured such that when the help button is selected in any appropriate manner, the power injector is temporarily disposed in a help mode (e.g., operation of the power injector may be temporarily suspended while the help functionality is enabled). Thereafter, selecting an object of the screen that is currently being presented on the first graphical user interface (e.g., a certain button; a certain parameter; a certain symbol; a certain graphical representation) will result in the presentation of help information on the first graphical user interface that pertains to the selected object. The help functionality and/or suspended status of the power injector may be terminated in any appropriate manner (e.g., selecting a "close" button or the like that may appear on the first graphical user interface in conjunction with the displayed help information). Terminating the help functionality may return the power injector to any appropriate state (e.g., the state of the power injector when help information was originally requested). The various "selections" referenced in relation to this thirteenth aspect may be executed in any appropriate manner, such as by touching the first graphical user interface (e.g., in the case where the first graphical user interface is in the form of a touch screen display), "clicking" a mouse at an appropriate location on the screen being presented on the first graphical user interface, or the like.

A fourteenth aspect of the present invention is embodied by a method of operating a power injector. A help button or the like on a screen being presented on a first graphical user interface may be selected in any appropriate manner (e.g., in the manner discussed above in relation to the thirteenth aspect). This may temporarily dispose the power injector in a help mode (e.g., operation of the power injector may be temporarily suspended while the help functionality is enabled). The user may then request help information on various different items on a screen that is currently being displayed on the first graphical user interface, and the requested help information may be displayed on the first graphical user interface in any appropriate manner. The help functionality and/or suspended status of the power injector may be terminated in any appropriate manner (e.g., selecting a "close" button or the like that may appear on the first graphical user interface in conjunction with the displayed help information). Terminating the help functionality may return the power injector to any appropriate state (e.g., the state of the power injector when help information was requested).

Various refinements exist of the features noted in relation to each of the above-noted first through the fourteenth aspects of the present invention. Further features may also be incorporated in each of the above-noted first through the fourteenth aspects of the present invention as well. These refinements and additional features may exist individually or in any desired combination in relation to each of the first through the fourteenth aspects. That is, each of the following features that will be discussed is not required to be used with any other feature or combination of features unless otherwise specified.

The power injector may be of any appropriate size, shape, configuration, and/or type. The power injector may utilize one or more syringe plunger drive assemblies or drivers of any appropriate size, shape, configuration, and/or type, where each such syringe plunger driver is capable of at least bi-directional movement (e.g., a movement in a first direction for discharging fluid; a movement in a second direction for accommodating a loading of fluid or so as to return to a position for a subsequent fluid discharge operation), and where each such syringe plunger driver may interact with its corresponding syringe plunger in any appropriate manner (e.g., by mechanical contact; by an appropriate coupling (mechanical or otherwise)) so as to be able to advance the syringe plunger in at least one direction (e.g., to discharge fluid). The power injector may be used for any appropriate application where the delivery of one or more medical fluids is desired and in any appropriate manner (e.g., via injection into a fluid target such as a patient), including without limitation any appropriate medical application (e.g., computed tomography or CT imaging; magnetic resonance imaging or MRI; SPECT imaging; PET imaging; X-ray imaging; angiographic imaging; optical imaging; ultrasound imaging). The power injector may be used in conjunction with any component or combination of components, such as an appropriate imaging system (e.g., a CT scanner). For instance, information could be conveyed between the power injector and one or more other components (e.g., scan delay information, injection start signal, injection rate).

Any appropriate number of syringes may be utilized with the power injector in any appropriate manner (e.g., detachably; front-loaded; rear-loaded; side-loaded), any appropriate medical fluid may be discharged from a given syringe of the power injector (e.g., contrast media, a radiopharmaceutical, saline, and any combination thereof), and any appropriate fluid may be discharged from a multiple syringe power injector configuration in any appropriate manner (e.g., sequentially, simultaneously), or any combination thereof. In one embodiment, fluid discharged from a syringe by operation of the power injector is directed into a conduit, where this conduit is fluidly interconnected with the syringe in any appropriate manner and directs fluid to a desired location (e.g., to a catheter that is inserted into a patient, for instance for injection).

The first graphical user interface may be associated with (e.g., incorporated on) the powerhead of the power injector. A console may be operatively interconnected with the powerhead and may be considered as a component of the power injector, and this console may incorporate the first graphical user interface. A first graphical user interface may be provided for each of the powerhead and a console. In one embodiment, the first graphical user interface is in the form of a touch screen display. Help information may be presented on the first graphical user interface by touching a certain portion or portions of the touch screen display. However, a mouse or any other appropriate way of making a selection on the first graphical user interface may be utilized.

Help information that is presented on the first graphical user interface may be in any appropriate form, such as a textual presentation, a graphical presentation, or a combination thereof. Help information may be presented on the first graphical user interface in response to requesting help on or through the first graphical user interface in any appropriate manner. For instance, a "help button" may be presented on the first graphical user interface. In one embodiment, selecting or activating any such help button temporarily disposes the power injector in a help mode, such that a subsequent selection of an object from the current screen on the first graphical user interface will display related help information. In another embodiment, selecting or activating any such help button may result in the presentation of an appropriate help screen on the first graphical user interface. In one embodiment, this help screen allows various help topics to be identified by reviewing a listing of help topics, by keyword searching, by keyword indexing, or a combination thereof.

A separate help icon or the like may be presented for one or more objects that are being presented on the first graphical user interface. Activating or selecting a particular help icon may result in the displaying of help information on the first graphical user interface that relates to the associated object. Each of a plurality of objects may include such a help icon, where activating or selecting a first help icon will present help information relating to a first object, and where activating or selecting a second help icon will present help information relating to a different, second object. Representative objects on the first graphical user interface screen for which help information may be retrieved include various parameters, data, designations, and buttons or keys.

DETAILED DESCRIPTION

Figure 1:
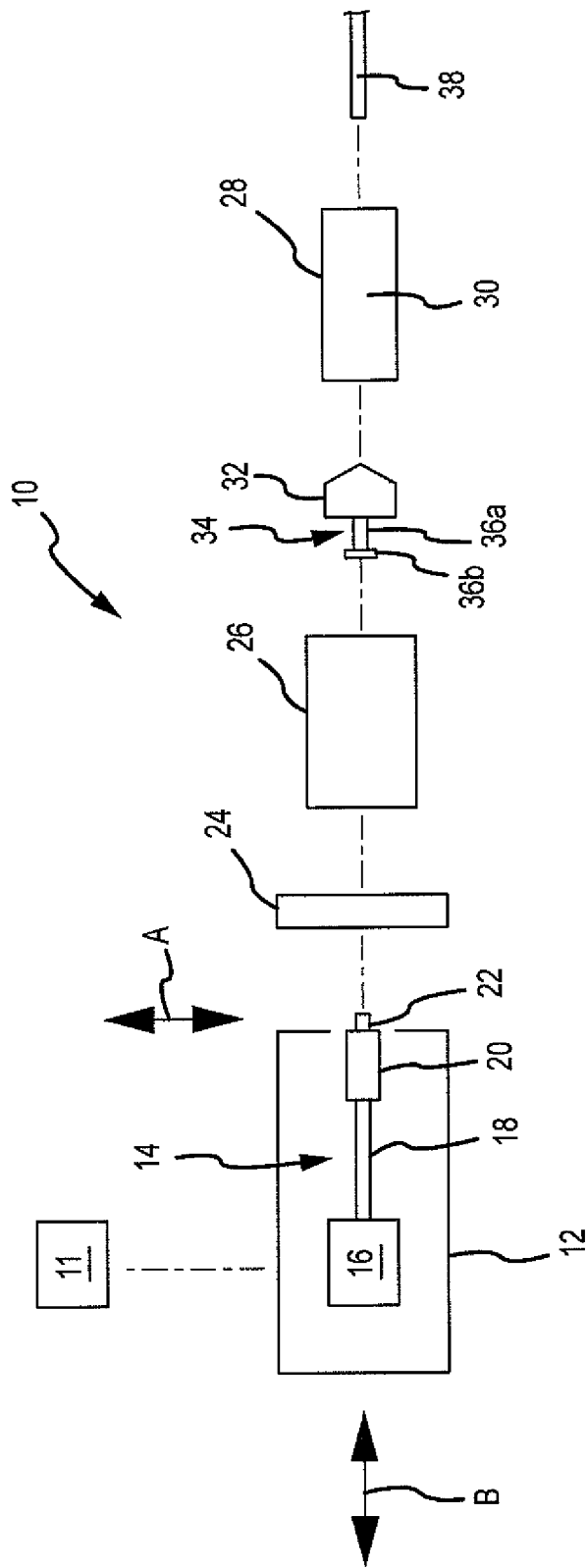
FIG. 1 is a schematic of one embodiment of a power injector.

FIG. 1 presents a schematic of one embodiment of a power injector 10 having a powerhead 12. One or more graphical user interfaces or GUIs 11 may be associated with the powerhead 12. Each GUI 11: 1) may be of any appropriate size, shape, configuration, and/or type; 2) may be operatively interconnected with the powerhead 12 in any appropriate manner; 3) may be disposed at any appropriate location; 4) may be configured to provide one or any combination of the following functions: controlling one or more aspects of the operation of the power injector 10; inputting/editing one or more parameters associated with the operation of the power injector 10; and displaying appropriate information (e.g., associated with the operation of the power injector 10); or 5) any combination of the foregoing. Any appropriate number of GUIs 11 may be utilized. In one embodiment, the power injector 10 includes a GUI 11 that is incorporated by a console that is separate from but which communicates with the powerhead 12. In another embodiment, the power injector 10 includes a GUI 11 that is part of the powerhead 12. In yet another embodiment, the power injector 10 utilizes one GUI 11 on a separate console that communicates with the powerhead 12, and also utilizes another GUI 11 that is on the powerhead 12. Each GUI 11 could provide the same functionality or set of functionalities, or the GUIs 11 may differ in at least some respect in relation to their respective functionalities.

A syringe 28 may be installed on this powerhead 12 and, when installed, may be considered to be part of the power injector 10. Some injection procedures may result in a relatively high pressure being generated within the syringe 28. In this regard, it may be desirable to dispose the syringe 28 within a pressure jacket 26. The pressure jacket 26 is typically associated with the powerhead 12 in a manner that allows the syringe 28 to be disposed therein as a part of or after installing the syringe 28 on the powerhead 12. The same pressure jacket 26 will typically remain associated with the powerhead 12, as various syringes 28 are positioned within and removed from the pressure jacket 26 for multiple injection procedures. The power injector 10 may eliminate the pressure jacket 26 if the power injector 10 is configured/utilized for low-pressure injections and/or if the syringe(s) 28 to be utilized with the power injector 10 is (are) of sufficient durability to withstand high-pressure injections without the additional support provided by a pressure jacket 26. In any case, fluid discharged from the syringe 28 may be directed into a conduit 38 of any appropriate size, shape, configuration, and/or type, which may be fluidly interconnected with the syringe 28 in any appropriate manner, and which may direct fluid to any appropriate location (e.g., to a patient).

The powerhead 12 includes a syringe plunger drive assembly 14 or driver that interacts (e.g., interfaces) with the syringe 28 (e.g., a plunger 32 thereof) to discharge fluid from the syringe 28. This syringe plunger drive assembly 14 includes a drive source 16 (e.g., a motor of any appropriate size, shape, configuration, and/or type, optional gearing, and the like) that powers a drive output 18 (e.g., a rotatable drive screw). A ram 20 may be advanced along an appropriate path (e.g., axial) by the drive output 18. The ram 20 may include a coupler 22 for interacting or interfacing with a corresponding portion of the syringe 28 in a manner that will be discussed below.

The syringe 28 includes a plunger or piston 32 that is movably disposed within a syringe barrel 30 (e.g., for axial reciprocation along an axis coinciding with the double-headed arrow B). The plunger 32 may include a coupler 34. This syringe plunger coupler 34 may interact or interface with the ram coupler 22 to allow the syringe plunger drive assembly 14 to retract the syringe plunger 32 within the syringe barrel 30. The syringe plunger coupler 34 may be in the form of a shaft 36a that extends from a body of the syringe plunger 32, together with a head or button 36b. However, the syringe plunger coupler 34 may be of any appropriate size, shape, configuration, and/or type.

Generally, the syringe plunger drive assembly 14 of the power injector 10 may interact with the syringe plunger 32 of the syringe 28 in any appropriate manner (e.g., by mechanical contact; by an appropriate coupling (mechanical or otherwise)) so as to be able to move or advance the syringe plunger 32 (relative to the syringe barrel 30) in at least one direction (e.g., to discharge fluid from the corresponding syringe 28). That is, although the syringe plunger drive assembly 14 may be capable of bi-directional motion (e.g., via operation of the same drive source 16), the power injector 10 may be configured such that the operation of the syringe plunger drive assembly 14 actually only moves each syringe plunger 32 being used by the power injector 10 in only one direction. However, the syringe plunger drive assembly 14 may be configured to interact with each syringe plunger 32 being used by the power injector 10 so as to be able to move each such syringe plunger 32 in each of two different directions (e.g. in different directions along a common axial path).

Retraction of the syringe plunger 32 may be utilized to accommodate a loading of fluid into the syringe barrel 30 for a subsequent injection or discharge, may be utilized to actually draw fluid into the syringe barrel 30 for a subsequent injection or discharge, or for any other appropriate purpose. Certain configurations may not require that the syringe plunger drive assembly 14 be able to retract the syringe plunger 32, in which case the ram coupler 22 and syringe plunger coupler 34 may not be desired. In this case, the syringe plunger drive assembly 14 may be retracted for purposes of executing another fluid delivery operation (e.g., after another pre-filled syringe 28 is installed). Even when a ram coupler 22 and syringe plunger coupler 34 are utilized, it may such that these components may or may not be coupled when the ram 20 advances the syringe plunger 32 to discharge fluid from the syringe 28 (e.g., the ram 20 may simply "push on" the syringe plunger coupler 34 or on a proximal end of the syringe plunger 32). Any single motion or combination of motions in any appropriate dimension or combination of dimensions may be utilized to dispose the ram coupler 22 and syringe plunger coupler 34 in a coupled state or condition, to dispose the ram coupler 22 and syringe plunger coupler 34 in an un-coupled state or condition, or both.

The syringe 28 may be installed on the powerhead 12 in any appropriate manner. For instance, the syringe 28 could be configured to be installed directly on the powerhead 12. In the illustrated embodiment, a housing 24 is appropriately mounted on the powerhead 12 to provide an interface between the syringe 28 and the powerhead 12. This housing 24 may be in the form of an adapter to which one or more configurations of syringes 28 may be installed, and where at least one configuration for a syringe 28 could be installed directly on the powerhead 12 without using any such adapter. The housing 24 may also be in the form of a faceplate to which one or more configurations of syringes 28 may be installed. In this case, it may be such that a faceplate is required to install a syringe 28 on the powerhead 12—the syringe 28 could not be installed on the powerhead 12 without the faceplate. When a pressure jacket 26 is being used, it may be installed on the powerhead 12 in the various manners discussed herein in relation to the syringe 28, and the syringe 28 will then thereafter be installed in the pressure jacket 26.

The housing 24 may be mounted on and remain in a fixed position relative to the powerhead 12 when installing a syringe 28. Another option is to movably interconnect the housing 24 and the powerhead 12 to accommodate installing a syringe 28. For instance, the housing 24 may move within a plane that contains the double-headed arrow A to provide one or more of coupled state or condition and an un-coupled state or condition between the ram coupler 22 and the syringe plunger coupler 34.

Figure 2A:
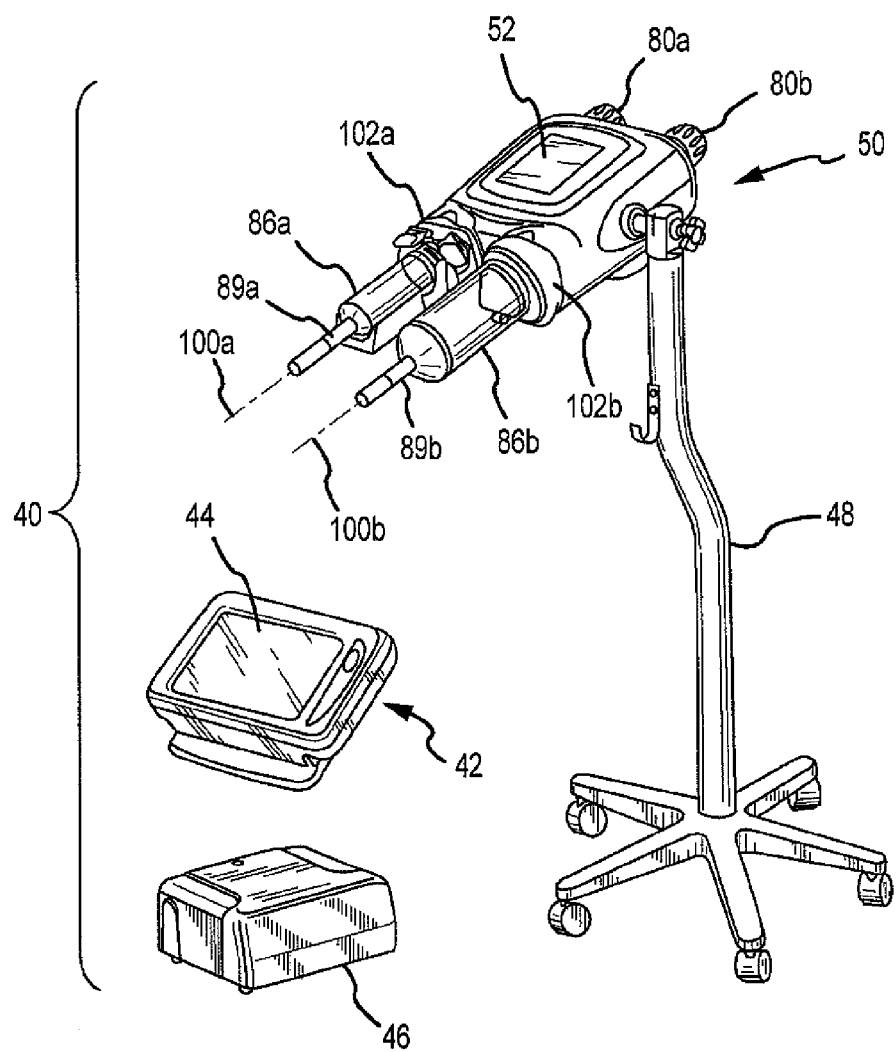
FIG. 2A is a perspective view of one embodiment of a portable stand-mounted, dual-head power injector.

One particular power injector configuration is illustrated in FIG. 2A, is identified by a reference numeral 40, and is at least generally in accordance with the power injector 10 of FIG. 1. The power injector 40 includes a powerhead 50 that is mounted on a portable stand 48. A pair of syringes 86a, 86b for the power injector 40 are mounted on the powerhead 50. Fluid may be discharged from the syringes 86a, 86b during operation of the power injector 40.

The portable stand 48 may be of any appropriate size, shape, configuration, and/or type. Wheels, rollers, casters, or the like may be utilized to make the stand 48 portable. The powerhead 50 could be maintained in a fixed position relative to the portable stand 48. However, it may be desirable to allow the position of the powerhead 50 to be adjustable relative to the portable stand 48 in at least some manner. For instance, it may be desirable to have the powerhead 50 in one position relative to the portable stand 48 when loading fluid into one or more of the syringes 86a, 86b, and to have the powerhead 50 in a different position relative to the portable stand 48 for performance of an injection procedure. In this regard, the powerhead 50 may be movably interconnected with the portable stand 48 in any appropriate manner (e.g., such that the powerhead 50 may be pivoted through at least a certain range of motion, and thereafter maintained in the desired position).

It should be appreciated that the powerhead 50 could be supported in any appropriate manner for providing fluid. For instance, instead of being mounted on a portable structure, the powerhead 50 could be interconnected with a support assembly, that in turn is mounted to an appropriate structure (e.g., ceiling, wall, floor). Any support assembly for the powerhead 50 may be positionally adjustable in at least some respect (e.g., by having one or more support sections that may be repositioned relative to one more other support sections), or may be maintained in a fixed position. Moreover, the powerhead 50 may be integrated with any such support assembly so as to either be maintained in a fixed position or so as to be adjustable relative the support assembly.

The powerhead 50 includes a graphical user interface or GUI 52. This GUI 52 may be configured to provide one or any combination of the following functions: controlling one or more aspects of the operation of the power injector 40; inputting/editing one or more parameters associated with the operation of the power injector 40; and displaying appropriate information (e.g., associated with the operation of the power injector 40). The power injector 40 may also include a console 42 and powerpack 46 that each may be in communication with the powerhead 50 in any appropriate manner (e.g., via one or more cables), that may be placed on a table or mounted on an electronics rack in an examination room or at any other appropriate location, or both. The powerpack 46 may include one or more of the following and in any appropriate combination: a power supply for the injector 40; interface circuitry for providing communication between the console 42 and powerhead 50; circuitry for permitting connection of the power injector 40 to remote units such as remote consoles, remote hand or foot control switches, or other original equipment manufacturer (OEM) remote control connections (e.g., to allow for the operation of power injector 40 to be synchronized with the x-ray exposure of an imaging system); and any other appropriate componentry. The console 42 may include a touch screen display 44, which in turn may provide one or more of the following functions and in any appropriate combination: allowing an operator to remotely control one or more aspects of the operation of the power injector 40; allowing an operator to enter/edit one or more parameters associated with the operation of the power injector 40; allowing an operator to specify and store programs for automated operation of the power injector 40 (which can later be automatically executed by the power injector 40 upon initiation by the operator); and displaying any appropriate information relation to the power injector 40 and including any aspect of its operation.

Figure 2B:
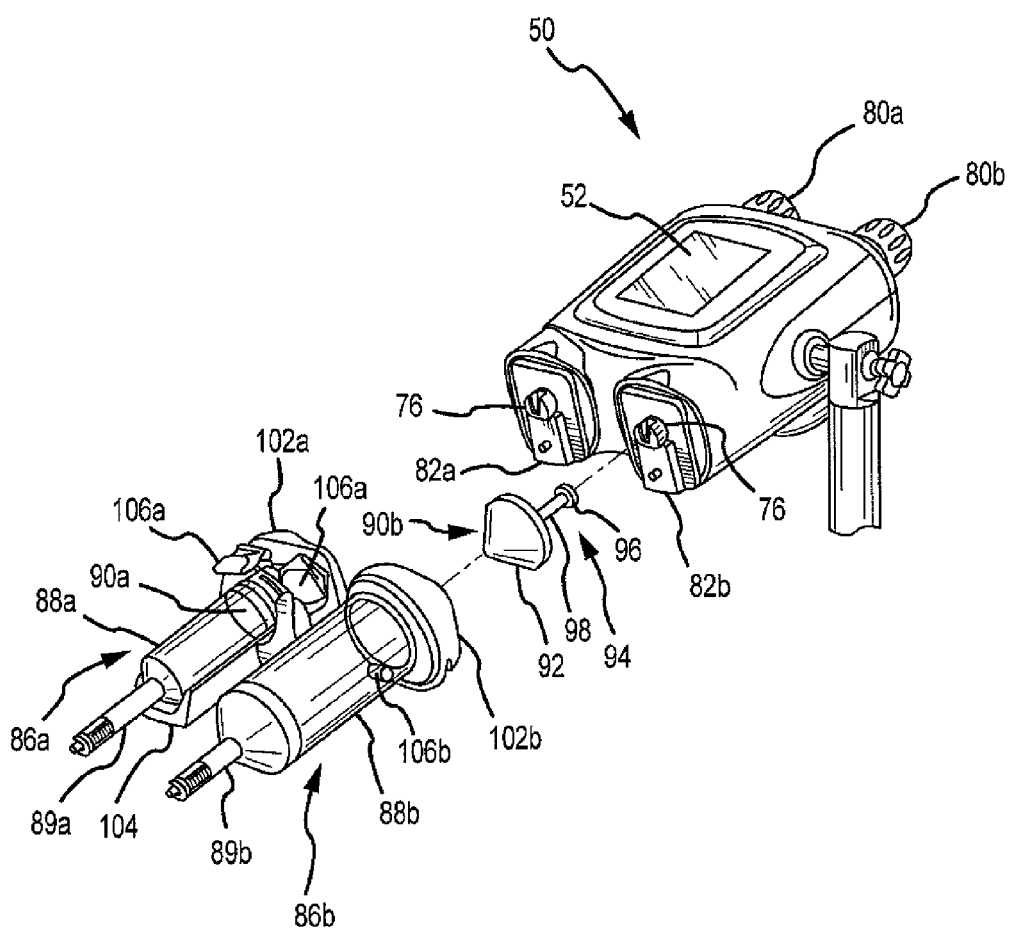
FIG. 2B is an enlarged, partially exploded, perspective view of a powerhead used by the power injector of FIG. 2A.

Various details regarding the integration of the syringes 86a, 86b with the powerhead 50 are presented in FIG. 2B. Each of the syringes 86a, 86b includes the same general components. The syringe 86a includes plunger or piston 90a that is movably disposed within a syringe barrel 88a. Movement of the plunger 90a along an axis 100a (FIG. 2A) via operation of the powerhead 50 will discharge fluid from within a syringe barrel 88a through a nozzle 89a of the syringe 86a. An appropriate conduit (not shown) will typically be fluidly interconnected with the nozzle 89a in any appropriate manner to direct fluid to a desired location (e.g., a patient). Similarly, the syringe 86b includes plunger or piston 90b that is movably disposed within a syringe barrel 86b. Movement of the plunger 90b along an axis 100b (FIG. 2A) via operation of the powerhead 50 will discharge fluid from within the syringe barrel 88b through a nozzle 89b of the syringe 86b. An appropriate conduit (not shown) will typically be fluidly interconnected with the nozzle 89b in any appropriate manner to direct fluid to a desired location (e.g., a patient).

The syringe 86a is interconnected with the powerhead 50 via an intermediate faceplate 102a. This faceplate 102a includes a cradle 104 that supports at least part of the syringe barrel 88a, and which may provide/accommodate any additional functionality or combination of functionalities. A mounting 82a is disposed on and is fixed relative to the powerhead 50 for interfacing with the faceplate 102a. A ram coupler 76 of a ram 74 (FIG. 2C), which are each part of a syringe plunger drive assembly 56 (FIG. 2C) for the syringe 86a, is positioned in proximity to the faceplate 102a when mounted on the powerhead 50. Details regarding the syringe plunger drive assembly 56 will be discussed in more detail below in relation to FIG. 2C. Generally, the ram coupler 76 may be coupled with the syringe plunger 90a of the syringe 86a, and the ram coupler 76 and ram 74 (FIG. 2C) may then be moved relative to the powerhead 50 to move the syringe plunger 90a along the axis 100a (FIG. 2A). It may be such that the ram coupler 76 is engaged with, but not actually coupled to, the syringe plunger 90a when moving the syringe plunger 90a to discharge fluid through the nozzle 89a of the syringe 86a.

The faceplate 102a may be moved at least generally within a plane that is orthogonal to the axes 100a, 100b (associated with movement of the syringe plungers 90a, 90b, respectively, and illustrated in FIG. 2A), both to mount the faceplate 102a on and remove the faceplate 102a from its mounting 82a on the powerhead 50. The faceplate 102a may be used to couple the syringe plunger 90a with its corresponding ram coupler 76 on the powerhead 50. In this regard, the faceplate 102a includes a pair of handles 106a. Generally and with the syringe 86a being initially positioned within the faceplate 102a, the handles 106a may be moved to in turn move/translate the syringe 86a at least generally within a plane that is orthogonal to the axes 100a, 100b (associated with movement of the syringe plungers 90a, 90b, respectively, and illustrated in FIG. 2A). Moving the handles 106a to one position moves/translates the syringe 86a (relative to the faceplate 102a) in an at least generally downward direction to couple its syringe plunger 90a with its corresponding ram coupler 76. Moving the handles 106a to another position moves/translates the syringe 86a (relative to the faceplate 102a) in an at least generally upward direction to uncouple its syringe plunger 90a from its corresponding ram coupler 76.

The syringe 86b is interconnected with the powerhead 50 via an intermediate faceplate 102b. A mounting 82b is disposed on and is fixed relative to the powerhead 50 for interfacing with the faceplate 102b. A ram coupler 76 of a ram 74 (FIG. 2C), which are each part of a syringe plunger drive assembly 56 for the syringe 86b, is positioned in proximity to the faceplate 102b when mounted to the powerhead 50. Details regarding the syringe plunger drive assembly 56 again will be discussed in more detail below in relation to FIG. 2C. Generally, the ram coupler 76 may be coupled with the syringe plunger 90b of the syringe 86b, and the ram coupler 76 and ram 74 (FIG. 2C) may be moved relative to the powerhead 50 to move the syringe plunger 90b along the axis 100b (FIG. 2A). It may be such that the ram coupler 76 is engaged with, but not actually coupled to, the syringe plunger 90b when moving the syringe plunger 90b to discharge fluid through the nozzle 89b of the syringe 86b.

The faceplate 102b may be moved at least generally within a plane that is orthogonal to the axes 100a, 100b (associated with movement of the syringe plungers 90a, 90b, respectively, and illustrated in FIG. 2A), both to mount the faceplate 102*b* on and remove the faceplate 102*b* from its mounting 82*b* on the powerhead 50. The faceplate 102*b* also may be used to couple the syringe plunger 90*b* with its corresponding ram coupler 76 on the powerhead 50. In this regard, the faceplate 102*b* may include a handle 106*b*. Generally and with the syringe 86*b* being initially positioned within the faceplate 102*b*, the syringe 86*b* may be rotated along its long axis 1006 (FIG. 2A) and relative to the faceplate 102*b*. This rotation may be realized by moving the handle 106*b*, by grasping and turning the syringe 86*b*, or both. In any case, this rotation moves/translates both the syringe 86*b* and the faceplate 102*b* at least generally within a plane that is orthogonal to the axes 100*a*, 100*b* (associated with movement of the syringe plungers 90*a*, 90*b*, respectively, and illustrated in FIG. 2A). Rotating the syringe 86*b* in one direction moves/translates the syringe 86*b* and faceplate 102*b* in an at least generally downward direction to couple the syringe plunger 90*b* with its corresponding ram coupler 76. Rotating the syringe 86*b* in the opposite direction moves/translates the syringe 86*b* and faceplate 102*b* in an at least generally upward direction to uncouple its syringe plunger 90*b* from its corresponding ram coupler 76.

As illustrated in FIG. 2B, the syringe plunger 90*b* includes a plunger body 92 and a syringe plunger coupler 94. This syringe plunger coupler 94 includes a shaft 98 that extends from the plunger body 92, along with a head 96 that is spaced from the plunger body 92. Each of the ram couplers 76 includes a larger slot that is positioned behind a smaller slot on the face of the ram coupler 76. The head 96 of the syringe plunger coupler 94 may be positioned within the larger slot of the ram coupler 76, and the shaft 98 of the syringe plunger coupler 94 may extend through the smaller slot on the face of the ram coupler 76 when the syringe plunger 90*b* and its corresponding ram coupler 76 are in a coupled state or condition. The syringe plunger 90*a* may include a similar syringe plunger coupler 94 for interfacing with its corresponding ram coupler 76.

Figure 2C:
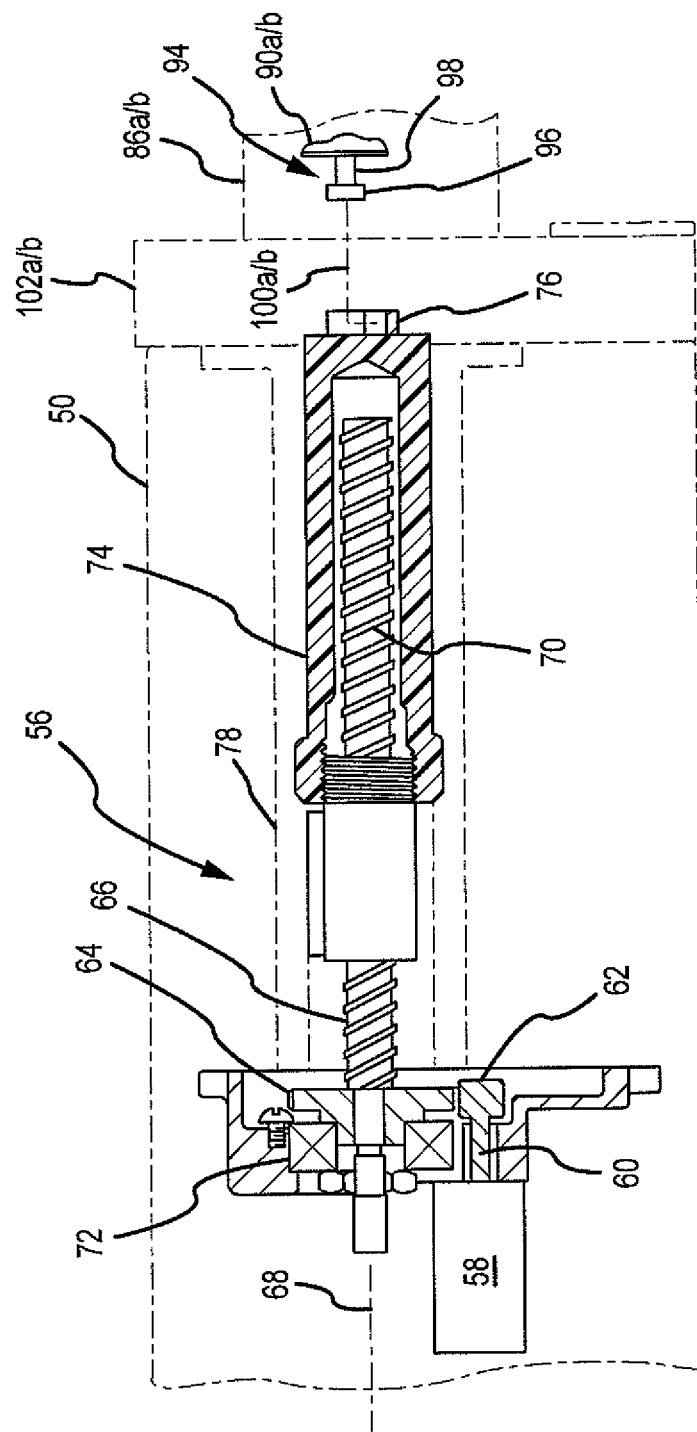
FIG. 2C is a schematic of one embodiment of a syringe plunger drive assembly used by the power injector of FIG. 2A.

The powerhead 50 is utilized to discharge fluid from the syringes 86*a*, 86*b* in the case of the power injector 40. That is, the powerhead 50 provides the motive force to discharge fluid from each of the syringes 86*a*, 86*b*. One embodiment of what may be characterized as a syringe plunger drive assembly is illustrated in FIG. 2C, is identified by reference numeral 56, and may be utilized by the powerhead 50 to discharge fluid from each of the syringes 86*a*, 86*b*. A separate syringe plunger drive assembly 56 may be incorporated into the powerhead 50 for each of the syringes 86*a*, 86*b*. In this regard and referring back to FIGS. 2A-B, the powerhead 50 may include hand-operated knobs 80*a* and 80*b* for use in separately controlling each of the syringe plunger drive assemblies 56.

Initially and in relation to the syringe plunger drive assembly 56 of FIG. 2C, each of its individual components may be of any appropriate size, shape, configuration and/or type. The syringe plunger drive assembly 56 includes a motor 58, which has an output shaft 60. A drive gear 62 is mounted on and rotates with the output shaft 60 of the motor 58. The drive gear 62 is engaged or is at least engageable with a driven gear 64. This driven gear 64 is mounted on and rotates with a drive screw or shaft 66. The axis about which the drive screw 66 rotates is identified by reference numeral 68. One or more bearings 72 appropriately support the drive screw 66.

A carriage or ram 74 is movably mounted on the drive screw 66. Generally, rotation of the drive screw 66 in one direction axially advances the ram 74 along the drive screw 66 (and thereby along axis 68) in the direction of the corresponding syringe 86*a/b*, while rotation of the drive screw 66 in the opposite direction axially advances the ram 74 along the drive screw 66 (and thereby along axis 68) away from the corresponding syringe 86*a/b*. In this regard, the perimeter of at least part of the drive screw 66 includes helical threads 70 that interface with at least part of the ram 74. The ram 74 is also movably mounted within an appropriate bushing 78 that does not allow the ram 74 to rotate during a rotation of the drive screw 66. Therefore, the rotation of the drive screw 66 provides for an axial movement of the ram 74 in a direction determined by the rotational direction of the drive screw 66.

The ram 74 includes a coupler 76 that that may be detachably coupled with a syringe plunger coupler 94 of the syringe plunger 90*a/b* of the corresponding syringe 86*a/b*. When the ram coupler 76 and syringe plunger coupler 94 are appropriately coupled, the syringe plunger 90*a/b* moves along with ram 74. FIG. 2C illustrates a configuration where the syringe 86*a/b* may be moved along its corresponding axis 100*a/b* without being coupled to the ram 74. When the syringe 86*a/b* is moved along its corresponding axis 100*a/b* such that the head 96 of its syringe plunger 90*a/b* is aligned with the ram coupler 76, but with the axes 68 still in the offset configuration of FIG. 2C, the syringe 86*a/b* may be translated within a plane that is orthogonal to the axis 68 along which the ram 74 moves. This establishes a coupled engagement between the ram coupler 76 and the syringe plunger coupler 96 in the above-noted manner.

The power injectors 10, 40 of FIGS. 1 and 2A-C each may be used for any appropriate application, including without limitation for medical imaging applications where fluid is injected into a subject (e.g., a patient). Representative medical imaging applications for the power injectors 10, 40 include without limitation computed tomography or CT imaging, magnetic resonance imaging or MRI, SPECT imaging, PET imaging, X-ray imaging, angiographic imaging, optical imaging, and ultrasound imaging. The power injectors 10, 40 each could be used alone or in combination with one or more other components. The power injectors 10, 40 each may be operatively interconnected with one or more components, for instance so that information may be conveyed between the power injector 10, 40 and one or more other components (e.g., scan delay information, injection start signal, injection rate).

Any number of syringes may be utilized by each of the power injectors 10, 40, including without limitation single-head configurations (for a single syringe) and dual-head configurations (for two syringes). In the case of a multiple syringe configuration, each power injector 10, 40 may discharge fluid from the various syringes in any appropriate manner and according to any timing sequence (e.g., sequential discharges from two or more syringes, simultaneous discharges from two or more syringes, or any combination thereof). Each such syringe utilized by each of the power injectors 10, 40 may include any appropriate fluid, for instance contrast media, a radiopharmaceutical, or saline. Each such syringe utilized by each of the power injectors 10, 40 may be installed in any appropriate manner (e.g., rear-loading configurations may be utilized; front-loading configurations may be utilized; side-loading configurations may be utilized).

Figure 3:
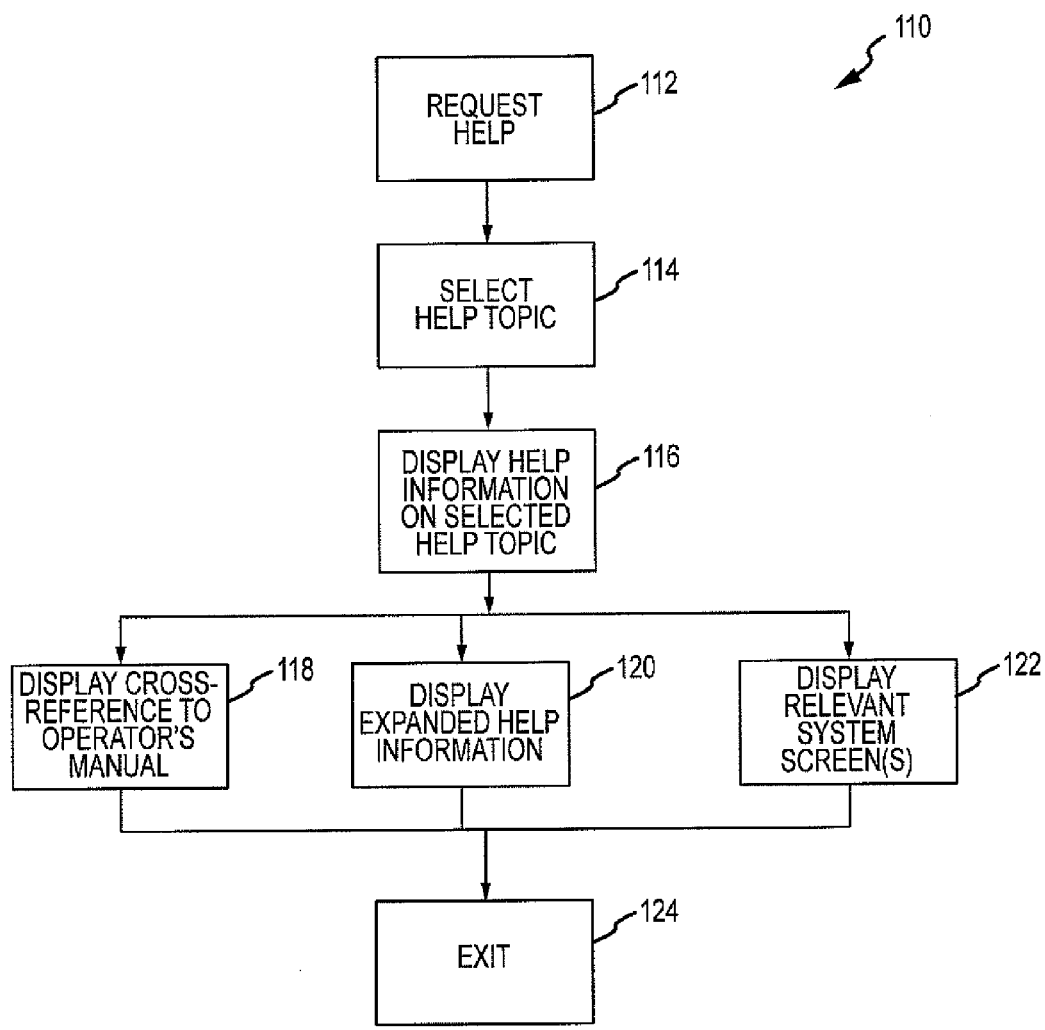
FIG. 3 is a schematic of one embodiment of a help protocol that may be utilized by a power injector, where one or more cross-references may be presented on a power injector graphical user interface on a selected help topic.

FIG. 3 presents one embodiment of a protocol 110 for providing power injector help functionality. The help protocol 110 may be incorporated by any appropriate power injector (e.g., power injector 10 of FIG. 1; power injector 40 of FIGS. 2A-C), and may be implemented in any appropriate manner (e.g., software, hardware, firmware, and any combination thereof). Hereafter, the help protocol 110 will be addressed in relation to the power injector 10 of FIG. 1. For convenience, the help protocol 110 will be discussed in relation to a single power injector graphical user interface 11, although the help protocol 110 could be course by implemented on multiple graphical user interfaces 11 if being utilized by the power injector 10. Generally, the help protocol 110 provides help functionality during the operation of the power injector 10 for a fluid (e.g., medical fluid) delivery operation or procedure. In this regard, the help protocol 110 may be characterized as being capable of temporarily placing the power injector 10 in a help mode versus an operational mode (e.g., operation of the power injector 10 may be characterized as being temporarily suspended during execution of the help protocol 110). After the desired help information is obtained or otherwise, the power injector 10 may be returned to any appropriate state, including without limitation the state of the power inject 10 when the help protocol 110 was initiated.

The help protocol 110 includes a step 112 where help may be requested regarding one or more aspects of the power injector 10, along with a step 114 where a particular help topic or subject may be selected. Steps 112 and 114 may be executed in any appropriate manner, including simultaneously or sequentially and in any appropriate order. Help information on the selected help topic of step 114 (e.g., a help output) may be presented or displayed on a graphical user interface 11 of the power injector 10 through execution of step 116 of the help protocol 110. This presentation of help information from step 116 may be in any form, including without limitation a textual description on the selected help topic from step 114.

Multiple help outputs on the selected help topic from step 114 may be presented on a power injector graphical user interface 11 through the help protocol 110 of FIG. 3. One or more cross-references may be provided in relation to the help information that is presented through execution of step 116. Each cross-reference may somehow pertain to the help information that is presented by step 116 of the help protocol 110.

A cross-reference to one or more relevant section(s) of an operator's manual for the power injector 10 may be provided on a power injector graphical user interface 11. This particular cross-reference may be provided through execution of step 118 of the help protocol 110 of FIG. 3 based upon the selected help topic of step 114, including without limitation where a cross-reference is provided to each relevant section of the operator's manual. In one embodiment, the operators manual for the power injector 10 is stored electronically and is accessible through a power injector graphical user interface 11. In this case, the cross-reference may be in the form of an electronic link(s) that is presented on a power injector graphical user interface 11 and that may be activated/selected in any appropriate manner (e.g., through touching an appropriate area on the graphical user interface 11; using a mouse associated with the graphical user interface 11). In another embodiment, a hard copy of the operators manual for the power injector 10 may be utilized by the help protocol 110, in which case the cross-reference to the relevant section(s) of the operators manual for the power injector 10 pursuant to step 118 of the help protocol 110 of FIG. 3 need not be active, but simply may be in the form of a display or an identification of the relevant section(s).

The help information that is displayed pursuant to step 116 of the help protocol 110 of FIG. 3 may be of a first level of detail. A second, higher level of detail on the selected help topic from step 114 may be presented on a power injector graphical user interface 11 through execution of step 120 (e.g., another help output). This more detailed information from step 120 may be accessed in any appropriate manner, may be of any appropriate form, and may be presented in any appropriate manner. In one embodiment, an appropriate icon or the like (e.g., an expand button) is presented along with the help information provided through execution of step 116, and when selected or activated in any appropriate manner produces the more detailed or expanded help information associated with step 120.

The help information that is presented through execution of step 116 of the help protocol 110 of FIG. 3 may be in any appropriate form as previously noted. Yet another cross-reference or related help output that may be beneficial is in the form of the system screen or screens that relate to the selected help topic of step 114, and that would be presented on a power injector graphical user interface 11 during operation of the power injector 10 to deliver fluid. This particular cross-reference or help output is provided through execution of step 122 of the help protocol 110. The relevant system screen or screens associated with step 122 may be presented at any appropriate time and the generation of each such screen may be initiated in any appropriate manner. In one embodiment, an appropriate icon or the like is presented along with the help information provided through step 116, and when selected or activated in any appropriate manner produces the associated system screen or screen(s) from step 122. In another embodiment, the help information from step 116 is presented within one window or in one area of a power injector graphical user interface 11, while the relevant system screen(s) is presented within another window or in another area of the same power injector graphical user interface 11.

Steps 116, 118, 120, and 122 of the help protocol 110 of FIG. 3 each may present what may be characterized as a help output. Therefore, the help protocol 110 may be characterized as providing multiple help outputs on the selected help topic from step 114. Any two or more of these help outputs may be presented in any appropriate manner and in any appropriate sequence. Steps 118, 120, and 122 each may be characterized as presenting a cross-reference to the help information that is presented on a power injector graphical user interface 11 through execution of step 116. Any one or more of the cross-references from steps 118, 120, and 122 may be utilized by the help protocol 110, each such cross-reference may be presented in any appropriate manner, and each such cross-reference may be presented in any appropriate sequence.

The help protocol 110 of FIG. 3 may be terminated by one or more exit steps 124 included at any appropriate location within the help protocol 110. This termination function of step 124 may be accessed/initiated in any appropriate manner. For instance, the screen on the power injector graphical user interface 11 that presents one or more help outputs from the help protocol 110 may include a "close button," an "OK button," or the like, and which may be selected/activated in any appropriate manner. The termination step 124 may return control to any appropriate screen on the power injector graphical user interface 11 (e.g., the system screen that was being presented when the help protocol 110 was initiated; the system screen associated with the current state of the power injector 10; the system screen that is displayed in accordance with step 122 of the help protocol 110 of FIG. 3).

Figure 4A:
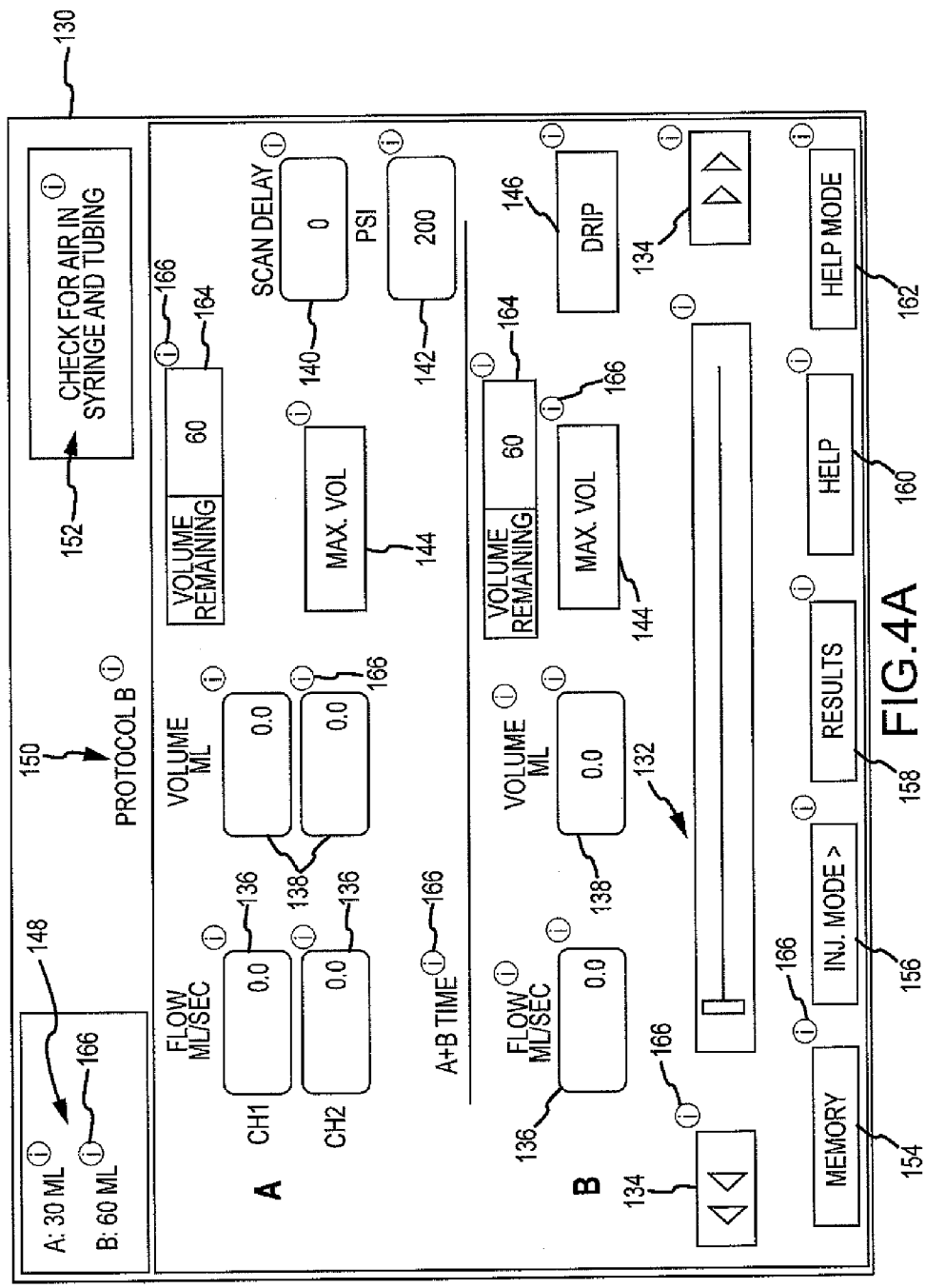
FIG. 4A is one embodiment of a setup screen for a power injector graphical user interface, and that may incorporate/embody one or more aspects of the help protocol of FIG. 3.

Any appropriate way for requesting help and selecting a particular help topic or subject for purposes of steps 112 and 114 of the help protocol 110 of FIG. 3 may be utilized. One embodiment of a setup screen is illustrated in FIG. 4A and is identified by reference numeral 130. This setup screen 130 may be presented on the graphical user interface 11 for the power injector 10 of FIG. 1, and is configured to execute each of steps 112 and 114 of the help protocol 110 of FIG. 3. Each system screen that is presented on the graphical user interface 11 for the power injector 10 of FIG. 1 may incorporate the features that will now be discussed with regard to the setup screen 130 of FIG. 4A for purposes of executing steps 112 and 114 of the help protocol 110 of FIG. 3.

The setup screen 130 of FIG. 4A is for the case of the power injector 10 of FIG. 1 being of a dual-head configuration—utilizing a pair of syringes 28 (one defining an A side of the power injector 10, and another defining a B side of the power injector 10). Each of the A and B sides may contain any appropriate fluid (e.g., contrast media, a radiopharmaceutical, saline, and any combination thereof). In addition, the setup screen 130 is configured for providing two phases on the A side of the power injector 10, and a single phase on the B side of the power injector 10. Any number of phases may be utilized by each of the A and B sides of the power injector 10, and the setup screen 130 may be configured accordingly. The power injector 10 may be configured to store multiple setup screens 130, each of which may use a different combination of phases for the A and B sides of the power injector 10.

Figure 7:
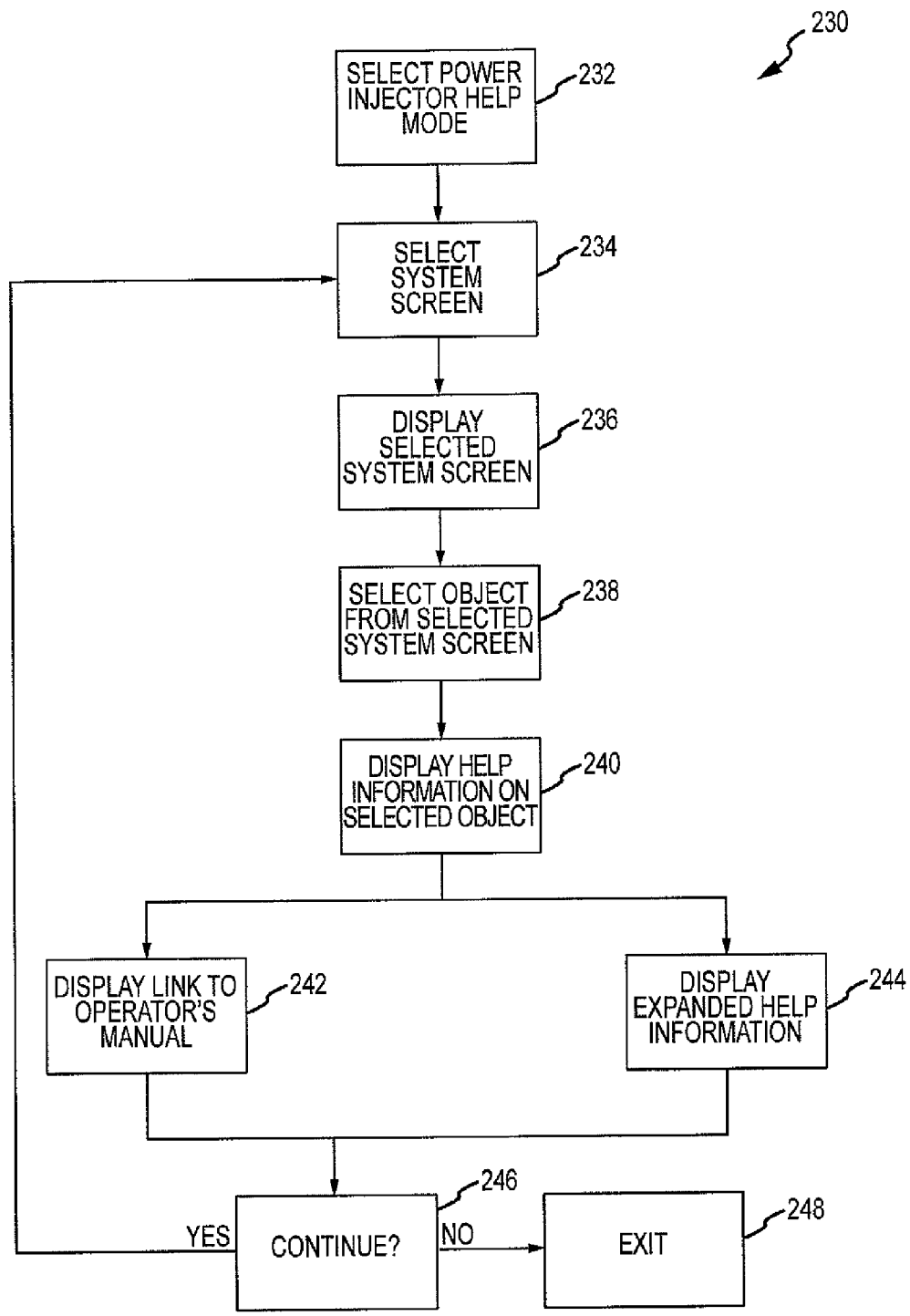
FIG. 7 is a schematic of one embodiment of a help protocol that may be utilized by a power injector, and which allows for an "off-line" review of one or more system screens that may be presented on a power injector graphical user interface while the power injector is being operated to deliver fluid.

The setup screen 130 of FIG. 4A may include various buttons to access various other system screens on the power injector graphical user interface 11, including a memory button 154 (e.g., for accessing an injection protocol that is stored), an injection mode button 156 (e.g., for selecting from a plurality of injection modes, where each injection mode has at least one phase for the A side and at least one phase for the B side), a results button 158 (e.g., for displaying results on an injection procedure), a help button 160 (e.g., for initiating the help protocol 110 of FIG. 3; for initiating the help protocol 190 of FIG. 5, discussed below), and a help mode button 162 (e.g., for operating the power injector 10 in a help mode, discussed below in relation to FIG. 7).

The setup screen 130 of FIG. 4A also includes the following: 1) a slide bar 132 for displaying/changing a value for a selected parameter presented on the setup screen 130; 2) adjustment arrows 134 for providing a more refined adjustment of a value for a selected parameter presented on the setup screen 130; 3) a pair of flow rate indicators 136 to depict the rate of delivery of contrast media from the A side of the power injector 10 (one for each of two phases), and another flow rate indicator 136 to depict the rate of delivery of saline from the B side of the power injector 10; 4) an injection volume indicator 138 to depict the volume to be injected from the syringe 28 for each of the A and B sides of the power injector 10; 5) a remaining volume indicator 164 to depict the projected volume remaining in the syringe 28 for each of the A and B sides of the power injector 10; 6) a scan delay indicator 140 to depict the time counted down from the start of an injection so that an operator may accurately delay a scanner being used in combination with the power injector 10; 7) a pressure limit indicator 142 for the syringe 28 on the A side of the power injector 10; 8) a maximum volume indicator 144 for each of the A and B sides of the power injector 10, which indicates the volume currently available in the associated syringe 28, and which may blank if the volume needed for an injection exceeds the available volume in the associated syringe 28; 9) a drip mode button or key 146 to access a drip mode functionality for the power injector 10 (e.g., a "drip injection" being a low flow rate injection of a small volume of fluid (e.g. saline) delivered to a patient in order to keep the fluid pathway to the patient in an open condition); 10) a pair of syringe size indicators 148 for each of the A and B sides of the power injector 10; 11) a protocol identifier 150 (e.g., to identify the protocol being used to operate the power injector 10); and 12) a message 152 (e.g., for an operator).

Step 112 of the help protocol 110 of FIG. 3 may be executed by selecting the help button or key 160 on the setup screen 130 of FIG. 4A. Selecting the help button 160 may temporarily dispose the power injector 10 into what may be characterized as a help mode (e.g., operation of the power injector 10 may be suspended at this time). Thereafter, help information could be displayed on the next portion of the setup screen 130 that is "selected" in any appropriate manner. In the case of the setup screen 130 being in the form of a touch screen display, a user could "touch" that part of the setup screen 130 on which the user desires to acquire help information (again, after having first selected the help button 160), and corresponding help information would then be displayed on the graphical user interface 11 (e.g., steps 114 and 116 of the help protocol 110 could be executed by simply touching the setup screen 130). A mouse of the like could also be used to request help information on a particular part of the setup screen 130. Help information may be made available in relation to any appropriate part of the setup screen 130 (e.g., buttons, parameters, symbols). Selecting the help button 160 also could result in the generation of a help screen (and could also again temporarily dispose the power injector 10 in a help mode), and which may then be used to execute step 114 of the help protocol 110 (e.g., help screen 170 of FIG. 4B, addressed below).

Steps 112 and 114 of the help protocol 110 of FIG. 3 may be simultaneously executed by selecting an information or help icon 166 from the setup screen 130 of FIG. 4A. An information icon 166 may be provided in relation to any one or more of the objects 132-162 presented on the setup screen 130 (e.g., an information icon 166 may be presented in relation to any displayed portion of the setup screen 130), including without limitation presenting an information icon 166 for each object presented on the setup screen 130. For instance, selecting the information icon 166 for a particular flow rate indicator 136 may display related help information pursuant to step 116 of the help protocol 110 of FIG. 3. Selecting the information icon 166 for the drip mode button 146 on the setup screen 130 may display related help information pursuant to step 116 of the help protocol of FIG. 3. Selection of an information icon 166 may also temporarily place the power injector 10 in a help mode.

Regardless of how help information is requested, the request for help and/or the provision of help information may temporarily dispose the power injector 10 in a help mode (e.g., operation of the power injector 10 may be temporarily suspended). The power injector 10 may be returned to any appropriate state (e.g., the state of the injector 10 when help was originally requested) in any appropriate manner and after the help functionality has been terminated in any appropriate manner (e.g., by a user selecting a "close" button or the like).

Figure 4B:
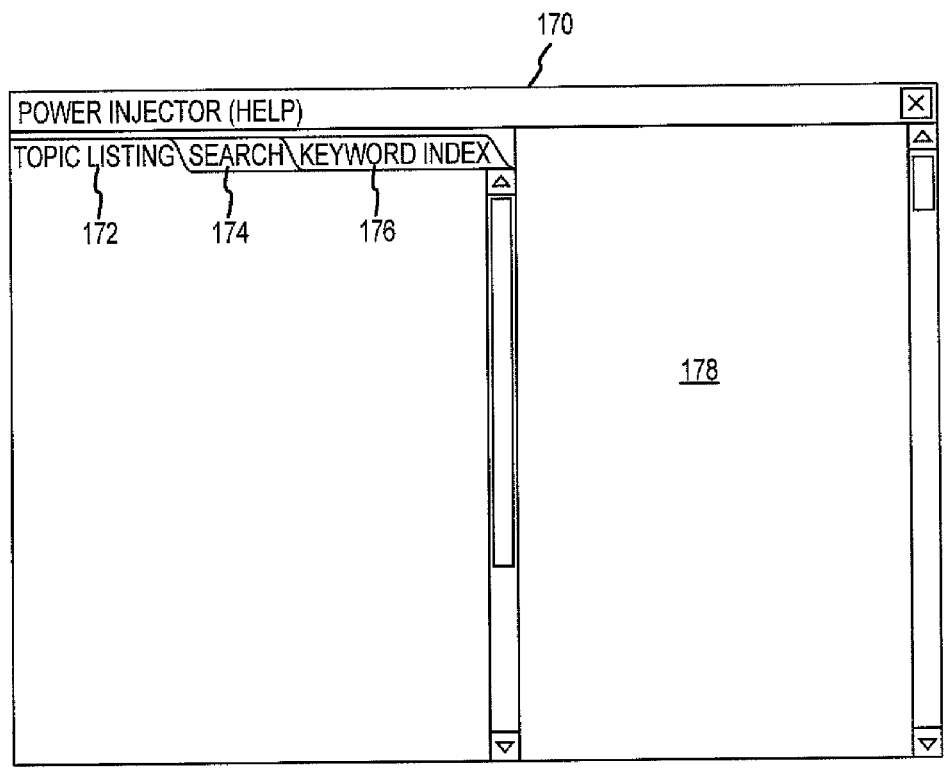
FIG. 4B is one embodiment of a help screen for a power injector graphical user interface, and that may incorporate/embody one or more aspects of the help protocol of FIG. 3.

FIG. 4B presents one embodiment of a help screen 170 that may be presented on a power injector graphical user interface 11. This type of the help screen 170 may be generated in response to an execution of step 112 of the help protocol 110 of FIG. 3, may be generated in response to selecting/activating the help button 160 on the setup screen 130 of FIG. 4A, or both. The help screen 170 may be of any appropriate configuration. Three different ways of identifying or selecting a particular help topic are provided by the help screen 170. The help screen 170 includes a help topic listing tab 172, a search tab 174, and a keyword Index tab 176. The help screen 170 could utilize any one or more of these tabs 172, 174, and 176.

Selecting or activating the topic listing tab 172 on the help screen 170 of FIG. 4B displays a list of help topics relating to the power injector 10. A particular help topic may be selected from this list in any appropriate manner. Selecting or activating the search tab 174 on the help screen 170 may display a data entry box or the like. One or more words may be entered in this data box, and may be used to search and identify relevant help topics. A particular help topic identified from the search may be selected in any appropriate manner. Selecting or activating the keyword index tab 176 on the help screen 170 may display a keyword index. A particular keyword or phrase may be input or selected in any appropriate manner to determine if this keyword or phrase is in the index. Regardless of how a help topic is identified and selected through the help screen 170, help information on the selected help topic may be displayed in a window 178 on the help screen 170 or on a completely separate screen (not shown). Moreover, one or more of the cross-references associated with steps 118, 120, and 122 of the help protocol 110 of FIG. 3 may be utilized in conjunction with the displayed help information.

Figure 4C:
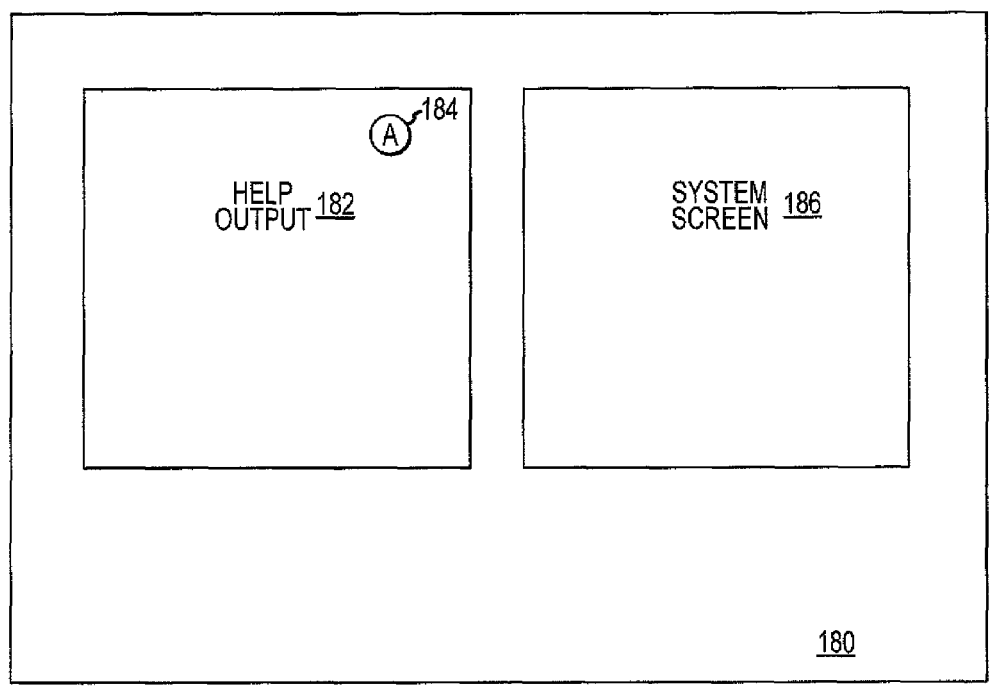
FIG. 4C is a representative help information display on a power injector graphical user interface.

Help information regarding the power injector 10 may be displayed on the power injector graphical user interface 11, including in accordance with the help protocol 110 of FIG. 3. FIG. 4C illustrates one embodiment of a graphical user interface output 180 that may be utilized to present help information. Information on a selected help topic may be presented in the form of a help output 182 in any appropriate form on the graphical user interface output 180. For instance, the help output 182 may be in the form of a textual description. In one embodiment, at least one system screen 186 that relates to the selected help topic is simultaneously presented along with the help output 182. This system screen 186 is one that would typically be presented on the graphical user interface 11 during an operation of the power injector 10 for purposes of delivering a fluid (e.g., an injection procedure). However, the relevant system screen 186 may be presented on another basis.

The help output 182 shown in FIG. 4C also includes an optional cross-reference selector or icon 184 of any appropriate size, shape, configuration, and/or type. Multiple cross-reference selectors 184 could be utilized as well. A cross-reference selector 184 could be in the form of and/or could be utilized to provide one or more of the following functions: 1) to generate the system screen 186, either alongside the help output 182, or as a separate graphical user interface output on the power injector graphical user interface 11 (not shown); 2) to display a cross-reference to at least one (and possibly each) relevant section of the operator's manual for the power injector 10; 3) to display an electronic link to at least one (and possibly each) relevant section of an electronically stored operators manual for the power injector 10, which may be selected and that will automatically bring up the relevant section(s); or 4) to provide expanded or more detailed information on the help topic from which the help output 182 was produced.

Figure 5:
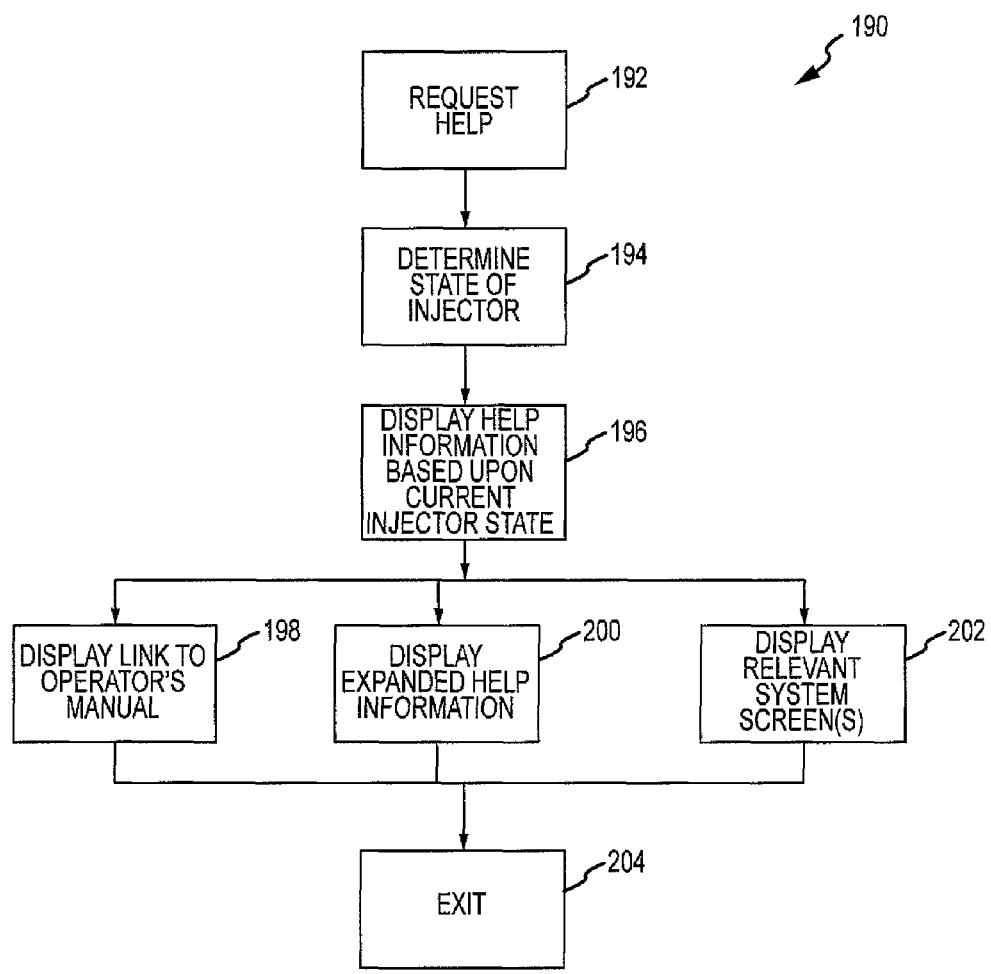
FIG. 5 is a schematic of one embodiment of a help protocol that may be utilized by a power injector, and which is based upon a current state of the power injector.

FIG. 5 presents one embodiment of a protocol 190 for providing power injector help functionality. The help protocol 190 may be incorporated by any appropriate power injector (e.g., power injector 10 of FIG. 1; power injector 40 of FIGS. 2A-C), and may be implemented in any appropriate manner. Hereafter, the help protocol 190 will be addressed in relation to the power injector 10 of FIG. 1. For convenience, the help protocol 190 will be discussed in relation to a single power injector graphical user interface 11, although the help protocol 190 could be course by implemented on multiple graphical user interfaces 11 if being utilized by the power injector 10.

The help protocol 190 includes a step 192, where help may be requested in any appropriate manner. For instance, a help button 160 on a screen currently being presented on the power injector graphical user interface 11 may be selected/activated in any appropriate manner (e.g., help button 160 on the setup screen 130 of FIG. 4A). Once help is requested through execution of step 192, the state of the power injector 10 is determined through execution of step 194. Representatives states of the power injector 10 can include without limitation that the power injector 10 is powered on and that no syringes 28 are installed on the powerhead 12, that at least one syringe 28 is installed on the powerhead 12, that the powerhead 12 is in a tilted up position, that an air purge operation is being executed, that an air purge operation has been completed, that the powerhead 12 is in a tilted down position, that the power injector 10 is ready to be enabled, that the power injector 10 is enabled, that a patency check injection is being executed, that a patency check has been completed, that a drip mode injection is being executed, that a drip mode injection has been terminated, that a timing bolus injection is being executed, that a timing bolus injection has been completed, that an injection is being executed, that an injection has been interrupted, that an injection has failed, that an injection has been completed, that each syringe 28 has been removed from the powerhead 12, that a "return syringe plunger drive assembly 14 to a home position" operation is being executed, and that the power injector 10 is ready to accept a number of syringes 28 for which the power injector 10 is configured. The power injector 10 could be in any one of multiple states while a single system screen is being presented on the power injector graphical user interface 11. The state of the power injector 10 may be determined in any appropriate manner.

Determination of the state of the power injector 10 through execution of step 194 of the help protocol 190 of FIG. 5 results in help information being displayed on the power injector graphical user interface 11 through execution of step 196, and which may be characterized as a help output. The help information that is displayed through execution of step 196 will relate to the current state of the power injector 10, may be of any appropriate form, and may be presented in any appropriate manner.

Multiple help outputs may be presented on a power injector graphical user interface 11 through the help protocol 190 of FIG. 5. Stated another way, one or more cross-references may be provided in relation to the help information that is presented through execution of step 196. Each cross-reference may somehow pertain to the help information that is presented by step 196 of the help protocol 190.

A cross-reference to one or more relevant section(s) of an operators manual for the power injector 10 may be provided on a power injector graphical user interface 11. This particular cross-reference may be provided through execution of step 198 of the help protocol 190 of FIG. 5 based upon the help information that is presented through execution of step 196, including without limitation where a cross-reference is provided to each relevant section of the operators manual. In one embodiment, the operators manual for the power injector 10 is stored electronically and is accessible through a power injector graphical user interface 11. In this case, the cross-reference may be in the form of an electronic link(s) that is presented on a power injector graphical user interface 11 and that may be activated in any appropriate manner (e.g., through touching an appropriate area on the graphical user interface 11; using a mouse associated with the graphical user interface 11). In another embodiment, a hard copy of the operators manual for the power injector 10 may be utilized by the help protocol 190, in which case the cross-reference to the relevant section of the operators manual for the power injector 10 pursuant to step 198 of the help protocol 190 of FIG. 5 need not be active, but simply may be in the form of a display or an identification of the relevant section(s).

The help information that is displayed pursuant to step 196 of the help protocol 190 of FIG. 5 may be of a first level of detail. A second, higher level of detail on the help information from step 196 may be presented on a power injector graphical user interface 11 through execution of step 200 (e.g., another help output). This more detailed information from step 200 may be accessed in any appropriate manner, may be of any appropriate form, and may be presented in any appropriate manner. In one embodiment, an appropriate icon or the like (e.g., an expand button) is presented along with the help information provided through step 196, and when selected or activated in any appropriate manner produces the more detailed or expanded help information associated with step 200.

The help information that is presented through execution of step 196 of the help protocol 190 of FIG. 5 may be in any appropriate form as noted. Yet another cross-reference or related help output that may be beneficial is in the form of the system screen or screens that relate to the help information provided by step 196, and that would be presented on a power injector graphical user interface 11 during operation of the power injector 10. This particular cross-reference or help output is provided through execution of step 202 of the help protocol 190. The relevant system screen or screens associated with step 202 may be presented at any appropriate time and initiated in any appropriate manner. In one embodiment, an appropriate icon or the like is presented along with the help information provided through step 196, and when selected or activated in any appropriate manner produces the associated system screen or screen(s) from step 202. In another embodiment, the help information from step 196 is presented within one window or in one area of the power injector graphical user interface 11, while the relevant system screen(s) is presented within another window or in another area of the power injector graphical user interface 11.

Steps 196, 198, 200, and 202 of the help protocol 190 of FIG. 5 each may present what may be characterized as a help output. Therefore, the help protocol 190 may provide multiple help outputs on a common help topic that is associated with the state of the power injector 10. Any two or more of these help outputs may be presented in any appropriate manner and in any appropriate sequence. Steps 198, 200, and 202 each may present what may be characterized as a cross-reference to the help information presented through execution of step 196. Any one or more of the cross-references from steps 198, 200, and 202 may be utilized by the help protocol 190, each such cross-reference may be presented in any appropriate manner, and each such cross-reference may be presented in any appropriate sequence.

The help protocol 190 of FIG. 5 may be terminated by one or more exit steps 204 included at any appropriate location within the help protocol 190. This termination function of step 204 may be accessed/initiated in any appropriate manner. For instance, the screen on the power injector graphical user interface 11 that presents one or more help outputs from the help protocol 190 may include a "close button," an "OK button," or the like, and which may be selected/activated in any appropriate manner. The termination step 204 may return control to any appropriate screen on the power injector graphical user interface 11 (e.g., the system screen that was being presented when the help protocol 190 was initiated; the system screen associated with the current state of the power injector 10).

Figure 6:
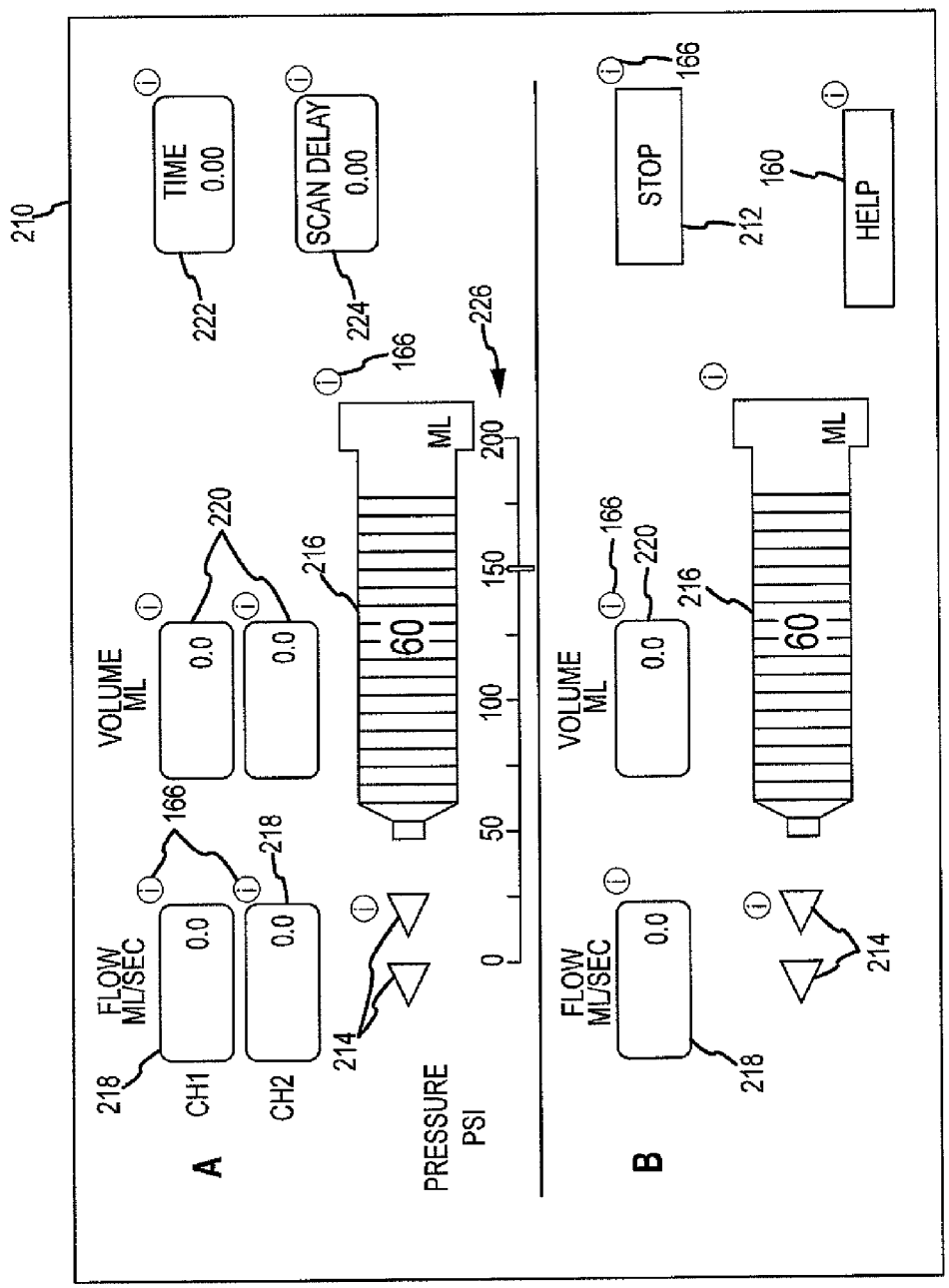
FIG. 6 is one embodiment of a progress screen for a power injector graphical user interface, and that may incorporate/embody one or more aspects of the help protocol of FIG. 5.

One embodiment of a progress screen is illustrated in FIG. 6, is identified by reference numeral 210, and is representative of a screen on a power injector graphical user interface 11 where the power injector 10 may be in any one of multiple states. The progress screen 210 of FIG. 6 is for the case of the power injector 10 of FIG. 1 being of a dual-head configuration—utilizing a pair of syringes 28 (one defining an A side of the power injector 10, and another defining a B side of the power injector 10). A representative listing of states that the power injector 10 may be in when the progress screen 210 is being displayed on the power injector graphical user interface 11 includes that a patency check injection is being executed, that a patency check has been completed, that a drip mode injection is being executed, that a drip mode injection has been terminated, that a timing bolus injection is being executed, that a timing bolus injection has been completed, that an injection is being executed, that an injection has been interrupted, that an injection has failed, that an injection has been completed, and that the power injector 10 has failed.

The progress screen 210 of FIG. 6 generally displays the progress of an injection procedure that is currently being performed by the power injector 10. Various buttons or keys that may be selected/activated in any appropriate manner may be included on the progress screen 210 to provide any appropriate function or combination of functions, including a stop button 212 (e.g., to stop operation of the power injector 10, or more specifically the delivery of fluid from the power injector 10), as well as a help button 160 (e.g., for initiating the help protocol 110 of FIG. 3; for initiating the help protocol 190 of FIG. 5). The progress screen 210 also includes the following: 1) injection indicators 214 for each of the A and B sides of the power injector 10, and which may flash to indicate when fluid is being delivered from the corresponding side; 2) a remaining volume indicator 216 for each of the A and B sides of the power injector 10, and which indicates the amount of volume remaining in the associated syringe 28; 3) a programmed flow indicator 218 for each of the two phases being utilized by the protocol on the A side of the power injector 10, and a programmed flow indicator 218 for the B side of the power injector 10, where each programmed flow indicator 218 displays the corresponding programmed flow rate for the current protocol being executed by the power injector 10; 4) a programmed volume indicator 220 for each of the two phases being utilized by the protocol on the A side of the power injector 10, and a programmed volume indicator 220 for the B side of the power injector 10, where each programmed volume indicator 220 displays the corresponding programmed volume for the current protocol being executed by the power injector 10; 5) an elapsed time indicator 222 that depicts the amount of time that has passed from the start of the injection procedure; 6) a scan delay indicator 224 to depict the time counted down from the start of an injection so that an operator may accurately delay a scanner being used in combination with the power injector 10; and 7) a pressure indicator 226 that may show the current pressure and the pre-set pressure limit value (the vertical line representing the pre-set pressure limit value, and the horizontal line representing the current pressure).

As in the case of the setup screen 130 of FIG. 4A, the progress screen 210 includes an information or help icon 166 for any one or more of the objects 212-226 presented on the progress screen 210 (e.g., an information icon 166 may be presented in relation to any displayed portion of the progress screen 210), including without limitation presenting an information icon 166 for each object presented on the progress screen 210. For instance, selecting the information icon 166 for a particular programmed flow indicator 218 may display related help information (e.g., pursuant to step 116 of the help protocol 110 of FIG. 3). Selecting the information icon 166 for the elapsed time indicator 222 on the progress screen 210 may display related help information (e.g., pursuant to step 116 of the help protocol of FIG. 3).

FIG. 7 presents one embodiment of a protocol 230 for providing power injector help functionality. The help protocol 230 may be incorporated by any appropriate power injector (e.g., power injector 10 of FIG. 1; power injector 40 of FIGS. 2A-C), and may be implemented in any appropriate manner (e.g., software, hardware, firmware, and any combination thereof). Hereafter, the help protocol 230 will be addressed in relation to the power injector 10 of FIG. 1. For convenience, the help protocol 110 will be discussed in relation to a single power injector graphical user interface 11, although the help protocol 110 could be course by implemented on multiple graphical user interfaces 11 if being utilized by the power injector 10.

The power injector 10 may be operated in what may be characterized as setup mode (e.g., where a protocol for controlling the execution of an injection procedure may be created, edited, and/or recalled from memory) and an injection or fluid delivery mode (e.g., where an injection procedure may be executed in accordance with a certain protocol). The help protocol 230 of FIG. 7 provides another mode of operation for the power injector 10. In this regard, step 232 is directing to selecting a help mode of operation for the power injector 10. Step 232 may be executed in any appropriate manner, for instance by selecting/activating a help mode button or key 162 on a system screen being presented on the power injector graphical user interface 11 (e.g., FIG. 4A). Once the help mode of operation is selected through step 232, a system screen is selected in step 234 of the help protocol 230 and is thereafter displayed on the power injector graphical user interface 11 through execution of step 236 of the help protocol 230.

A system screen for the power injector 10 may be selected in any appropriate manner for purposes of step 234 of the help protocol of FIG. 7. For instance and upon entering the help mode of operation for the power injector 10 through step 232, a listing of system screens could be provided in any appropriate manner, and a particular system screen may thereafter be selected in any appropriate manner. Another option would be to allow a user to simply scroll through the various system screens. In any case and with a system screen being displayed on the power injector graphical user interface 11 pursuant to step 236, one or more objects that are presented on this system screen may be selected in any appropriate manner through execution of step 238 of the protocol 230. For instance, an information icon 166 could be presented next to one or more textual and/or graphical representations included on the system screen (e.g., FIG. 4A), and which can be selected in any appropriate manner.

Selection of an object being presented on a system screen by the power injector graphical user interface 11 results in related help information being displayed through execution of step 240. This presentation of help information from step 240 may be in any form, including without limitation a textual description.

Multiple help outputs on a common help topic may be presented on a power injector graphical user interface 11 through the help protocol 230 of FIG. 7. Stated another way, one or more cross-references may be provided in relation to the help information that is presented through execution of step 240. Each cross-reference may somehow pertain to the help information that is presented by step 240 of the help protocol 230.

A cross-reference to one or more relevant section(s) of an operators manual for the power injector 10 may be provided on a power injector graphical user interface 11. This particular cross-reference may be provided through execution of step 242 of the help protocol 230 of FIG. 7 based upon the help information being displayed pursuant to step 240, including without limitation where a cross-reference is provided to each relevant section of the operators manual. In one embodiment, the operators manual for the power injector 10 is stored electronically and is accessible through a power injector graphical user interface 11. In this case, the cross-reference may be in the form of an electronic link(s) that is presented on a power injector graphical user interface 11 and that may be selected/activated in any appropriate manner (e.g., through touching an appropriate area on the graphical user interface 11; using a mouse associated with the graphical user interface 11). In another embodiment, a hard copy of the operators manual for the power injector 10 may be utilized by the help protocol 230, in which case the cross-reference to the relevant section of the operators manual for the power injector 10 pursuant to step 242 of the help protocol 230 of FIG. 7 need not be active, but simply may be in the form of a display or an identification of the relevant section(s).

The help information that is displayed pursuant to step 240 of the help protocol 230 of FIG. 7 may be of a first level of detail. A second, higher level of detail relating to the displayed help information from step 240 may be presented on a power injector graphical user interface 11 through execution of step 244 (e.g., another help output). This more detailed information from step 244 may be accessed in any appropriate manner, may be of any appropriate form, and may be presented in any appropriate manner. In one embodiment, an appropriate icon or the like (e.g., an expand button) is presented along with the help information provided through step 240, and when selected or activated in any appropriate manner produces the more detailed or expanded help information associated with step 244.

Help information may be retrieved in accordance with the foregoing for any one or more of the objects that are presented on the current system screen associated with step 234 and for which help information has been made available (e.g., by selecting or activating a "close button," an "OK button," or the like). Help information may be retrieved in accordance with the foregoing for each of the system screens being utilized by the power injector 10. For instance, step 246 of the help protocol 230 may return control to step 234, where another system may be selected in accordance with the foregoing. The help protocol 230 of FIG. 7 may be terminated by one or more exit steps 248 included at any appropriate location within the help protocol 230. This exit function of step 248 may be accessed/initiated in any appropriate manner. For instance, the screen on the power injector graphical user interface 11 that presents one or more help outputs from the help protocol 230 may include a "close button," an "OK button," or the like, and which may be selected/activated in any appropriate manner. The exit step 248 may return control to any appropriate screen on the power injector graphical user interface 11 (e.g., a main or startup screen for the power injector 10).

Figure 8:
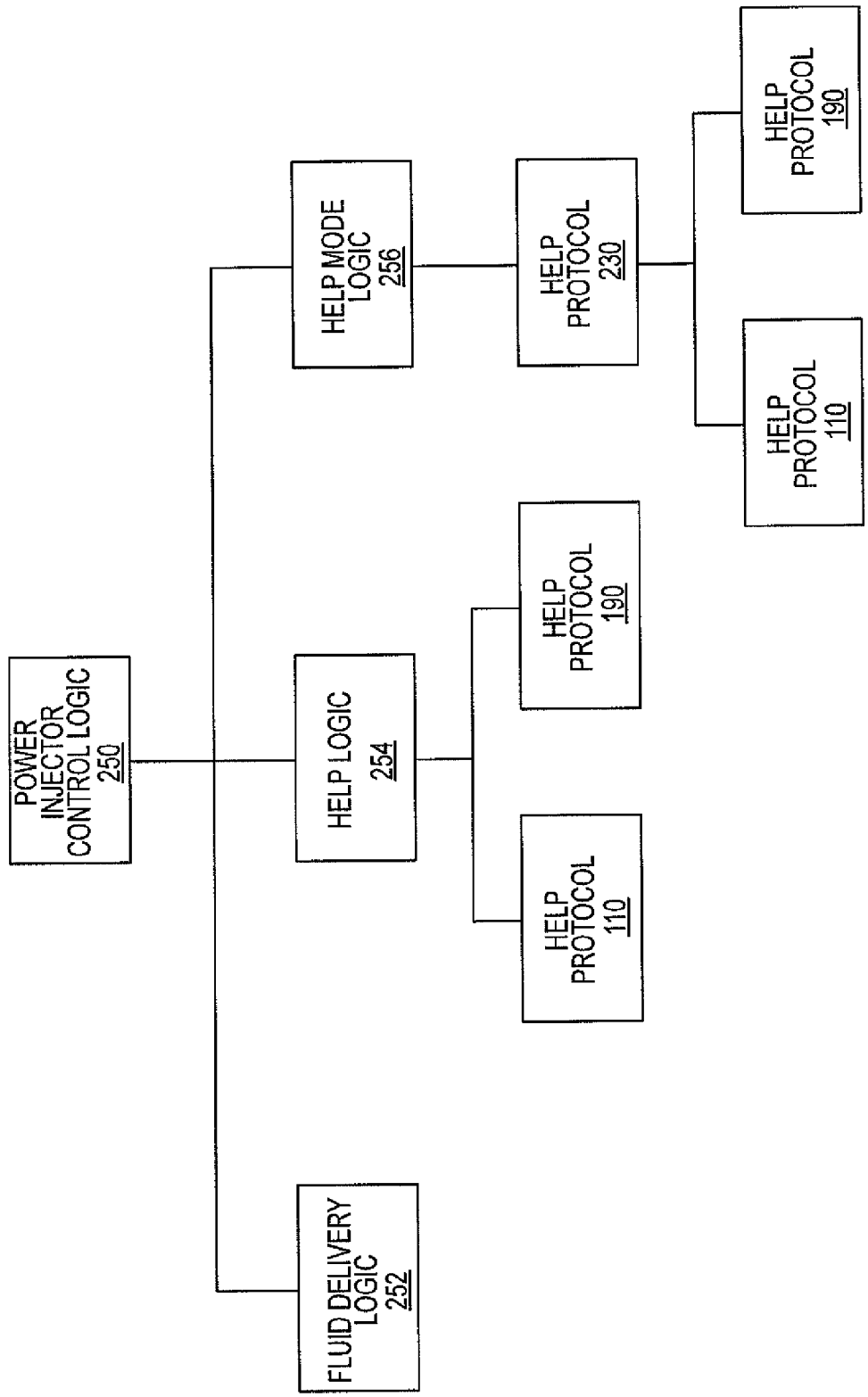
FIG. 8 is a schematic of one embodiment of power injector control logic that may be used by a power injector, and which may be configured to execute the help protocols of FIGS. 3, 5, and 7.

FIG. 8 presents one embodiment of power injector control logic 250 that may be utilized by any appropriate power injector. The power injector control logic 250 may be of any appropriate form and/or configuration, for instance software, may be implemented or integrated in any appropriate manner, or both (e.g., for instance in the power injector software; implemented by software, hardware, firmware, and any combination thereof). In one embodiment, the functionality of the control logic 250 is provided by one or more processors of any appropriate size, shape, configuration, and/or type. In one embodiment, the functionality of the control logic 250 is provided by one or more computers of any appropriate size, shape, configuration, and/or type.

The power injector control logic 250 includes fluid delivery logic 252, help logic 254, and help mode logic 256. The fluid delivery logic 252 may be utilized to control one or more aspects of the delivery of fluid by a power injector that utilizes the power injector control logic 250, including an injection procedure. For a medical fluid application, the logic 252 thereby may be referred to as medical fluid delivery logic 252 (e.g., for providing fluid to a fluid target, such as a patient (e.g., human, animal), including without limitation by injection). The help mode logic 254 may utilize one or more of the above-discussed help protocols 110 and 190. The help mode logic 256 may utilize the above-discussed help protocol 230, which in turn may utilize one or more of the above-discussed help protocols 110 and 190. The power injector control logic 250 may be of any appropriate configuration to provide the functionality associated with the fluid delivery logic 252, the help logic 254, and the help mode logic 256.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A power injector, comprising:
   a powerhead, wherein a syringe may be installed on said powerhead;
   a syringe plunger drive assembly;
   a first graphical user interface;
   a fluid delivery mode where fluid is delivered by said power injector;
   a help mode, wherein said fluid delivery mode is suspended such that fluid is not deliverable by said power injector when said power injector is in said help mode; and
   a help button, wherein activation of said help button suspends said fluid delivery mode and instead disposes said power injector in said help mode, wherein a selected help topic relates to at least one aspect of said power injector in conjunction with execution of a fluid delivery procedure, and wherein said selected help topic thereafter causes said help mode to generate each of the following on said first graphical user interface:
      a first help output that relates to said selected help topic;
      each system screen: i) that is presented on said first graphical user interface when said power injector is in said fluid delivery mode and while said power injector is executing a fluid delivery procedure; and ii) that relates to said selected help topic, wherein said first help output is separate from and in addition to each said system screen that is presented on said first graphical user interface while said power injector is in said help mode, and wherein each system screen that is generated on said first graphical user interface when said power injector is in said fluid delivery mode pertains to said power injector in conjunction with execution of said fluid delivery procedure; and
      at least one cross-reference that provides additional help information on said selected help topic:
   wherein said first help output is separate from and in addition to each said system screen that is presented on said first graphical user interface when said power injector is in said help mode;
   wherein each said system screen that is displayed on said first graphical user interface during operation of said power injector in said help mode is also displayed on said first graphical user interface during operation of said power injector in said fluid delivery mode; and
   wherein said first help output and one of said system screens are simultaneously presented on said first graphical user interface, from said power injector being in said help mode, and in response to said selected help topic.

2. The power injector of claim 1, wherein said activation of said help button presents a help screen on said first graphical user interface, wherein said help screen presents a plurality of help topics, and wherein said selected help topic is from said plurality of help topics and said selected help topic is generated by user input to said power injector.

3. The power injector of claim 1, wherein said selected help topic is based upon a current state of said power injector when said help button is activated.

4. The power injector of claim 3, wherein said current state is selected from the group consisting of that said power injector is powered on and that no syringes are installed on said powerhead, that at least one syringe is installed on said powerhead, that said powerhead is in a tilted up position, that an air purge operation is being executed, that an air purge operation has been completed, that said powerhead is in a tilted down position, that said power injector is ready to be enabled, that said power injector is enabled, that a patency check injection is being executed, that a patency check has been completed, that a drip mode injection is being executed, that a drip mode injection has been terminated, that a timing bolus injection is being executed, that a timing bolus injection has been completed, that an injection is being executed, that an injection has been interrupted, that an injection has failed, that an injection has been completed, that each syringe has been removed from said powerhead, that a "return each syringe plunger driver to a home position" operation is being executed, and that said power injector is ready to accept a number of syringes for which said power injector is configured.

5. The power injector of claim 1, further comprising:
   power injector control logic comprising a fluid delivery logic and a help mode logic, wherein said power injector may be separately operated in accordance with each of said fluid delivery mode logic and said help mode logic, and wherein fluid is not deliverable by said power injector when operating in accordance with said help mode logic.

6. The power injector of claim 5, wherein when said power injector is operated in accordance with said help mode logic, a first said system screen from when said power injector is operated in accordance with said fluid delivery logic is presentable on said first graphical user interface and comprises a plurality of selectable objects, and wherein separately selecting each said selectable object from said first said system screen on said first graphical user interface presents corresponding help information on said first graphical user interface, and wherein each said selectable object on said first said system screen may be selected to present said corresponding help information on said first graphical user interface.

7. The power injector of claim 5, wherein when said power injector is operated in accordance with said help mode logic, each said system screen from when said power injector is operated in accordance with said fluid delivery logic is presentable on said first graphical user interface and each said system screen comprises a plurality of selectable objects, and wherein separately selecting each said selectable object from said system screen currently being presented on said first graphical user interface presents corresponding help information on said first graphical user interface.

8. The power injector of claim 1, wherein said activation of said help button allows said selected help topic to be identified from a plurality of available help topics and with said selected help topic being based upon user input to said power injector.

9. The power injector of claim 1, wherein said first graphical user interface is on said powerhead.

10. The power injector claim 1, further comprising a console operatively interconnected with said powerhead, wherein said console comprises said first graphical user interface.

11. A power injector, comprising:
   a powerhead, wherein a syringe may be installed on said powerhead;
   a syringe plunger drive assembly;
   a first graphical user interface; and
   power injector control logic comprising a fluid delivery logic and a help mode logic, wherein said power injector may be separately operated in accordance with each of said fluid delivery mode logic and said help mode logic, wherein fluid is not deliverable by said power injector when operating in accordance with said help mode logic and disposes said power injector in a help mode, and wherein when said power injector is operated in accordance with said help mode logic:
      each system screen, from when said power injector is operated in accordance with said fluid delivery logic for execution of said fluid delivery procedure by said power injector, is presentable on said first graphical user interface prior to exiting said help mode and where each said system screen comprises a plurality of selectable objects with said power injector being in said help mode, wherein said power injector is configured to allow a user to access each said system screen having said plurality of selectable objects when said power injector is being controlled by said help mode logic and prior to exiting said help mode, and wherein each said system screen that is generated on said first graphical user interface when said power injector is in said fluid delivery mode pertains to said power injector in conjunction with execution of said fluid delivery procedure; and
      separately selecting each said selectable object from said system screen that is currently being presented on said first graphical user interface, pursuant to said help mode logic, defines a corresponding selected object and presents both a first help output and at least one cross-reference to additional help information on said first graphical user interface that each relate to said corresponding selected object and that are each presented on said first graphical user interface in response to said corresponding selected object.

12. The power injector of claim 11, wherein said at least one cross-reference comprises an identification of at least one section of an operator's manual for said power injector.

13. The power injector of claim 11, wherein said at least one cross-reference pertains to at least one section of an operator's manual for said power injector that relates to said corresponding selected object, wherein said operator's manual is electronically stored, and wherein said cross-reference comprises an electronic link to said at least one section of said operator's manual.

14. The power injector of claim 11, wherein said first help output comprises a first level of help information, and wherein said at least one cross-reference comprises a link to a second level of help information that is more detailed than said first level.

15. The power injector of claim 11, wherein said at least one cross-reference comprises an electronic link to said at least one section of an operator's manual for said power injector.

16. The power injector of claim 11, wherein said first graphical user interface is on said powerhead.

17. The power injector claim 11, further comprising a console operatively interconnected with said powerhead, wherein said console comprises said first graphical user interface.

* * * * *